(12) United States Patent
Some

(10) Patent No.: US 7,009,695 B2
(45) Date of Patent: Mar. 7, 2006

(54) FULL FRAME THERMAL PUMP PROBE TECHNIQUE FOR DETECTING SUBSURFACE DEFECTS

(75) Inventor: Daniel I. Some, Ashdod (IL)

(73) Assignee: Applied Materials, Inc., Santa Clara, CA (US)

( * ) Notice: Subject to any disclaimer, the term of this patent is extended or adjusted under 35 U.S.C. 154(b) by 9 days.

(21) Appl. No.: 10/812,817

(22) Filed: Mar. 29, 2004

(65) Prior Publication Data

US 2004/0196453 A1     Oct. 7, 2004

Related U.S. Application Data

(60) Provisional application No. 60/459,908, filed on Apr. 1, 2003.

(51) Int. Cl.
*G01N 21/88* (2006.01)

(52) U.S. Cl. .......................................... 356/237.1; 374/5

(58) Field of Classification Search .. 356/237.2–237.5, 356/237.1, 432; 374/4–5
See application file for complete search history.

(56) References Cited

U.S. PATENT DOCUMENTS

| | | | | |
|---|---|---|---|---|
| 4,679,946 A | * | 7/1987 | Rosencwaig et al. | 356/445 |
| 4,854,724 A | * | 8/1989 | Adams et al. | 374/5 |
| 5,099,363 A | * | 3/1992 | Lichtman | 359/235 |
| 5,131,755 A | | 7/1992 | Chadwick et al. | 356/394 |
| 5,292,195 A | * | 3/1994 | Crisman, Jr. | 374/4 |
| 5,450,205 A | | 9/1995 | Sawin et al. | 356/382 |
| 5,834,661 A | * | 11/1998 | Nonaka et al. | 374/5 |
| 5,917,588 A | | 6/1999 | Addiego | 356/237 |
| 5,962,862 A | | 10/1999 | Evers et al. | 250/559.4 |
| 6,297,879 B1 | | 10/2001 | Yang et al. | 356/237.5 |
| 6,585,146 B1 | * | 7/2003 | Shepard | 228/104 |
| 6,606,401 B1 | | 8/2003 | Sender | 382/144 |
| 2003/0099392 A1 | | 5/2003 | Levin et al. | 382/149 |
| 2003/0174878 A1 | | 9/2003 | Levin et al. | 382/149 |
| 2003/0206292 A1 | | 11/2003 | Some | 356/237.1 |

OTHER PUBLICATIONS

International Search Report in PCT/US04/09938 dated Mar. 18, 2005.
Written Opinion in PCT/US04/09938 dated Mar. 18, 2005.

* cited by examiner

*Primary Examiner*—Richard A. Rosenberger
(74) *Attorney, Agent, or Firm*—Omkar Suryadevara

(57) ABSTRACT

An area of a substrate is imaged with and without heating, to obtain a hot image and a cold image respectively. The hot and cold images are compared with one another to identify one or more locations as being defective, e.g. if the result of comparison at one location differs significantly relative to other locations. The comparison results in all locations form a differential image, and in several embodiments a number of differential images are obtained by repeatedly heating, imaging and comparing. In such embodiments, multiple differential images are averaged at each location, to improve the signal to noise ratio. Pump and probe lasers may be used for heating and for illumination respectively, or alternatively a single laser may be employed to generate both pump and probe beams.

48 Claims, 14 Drawing Sheets

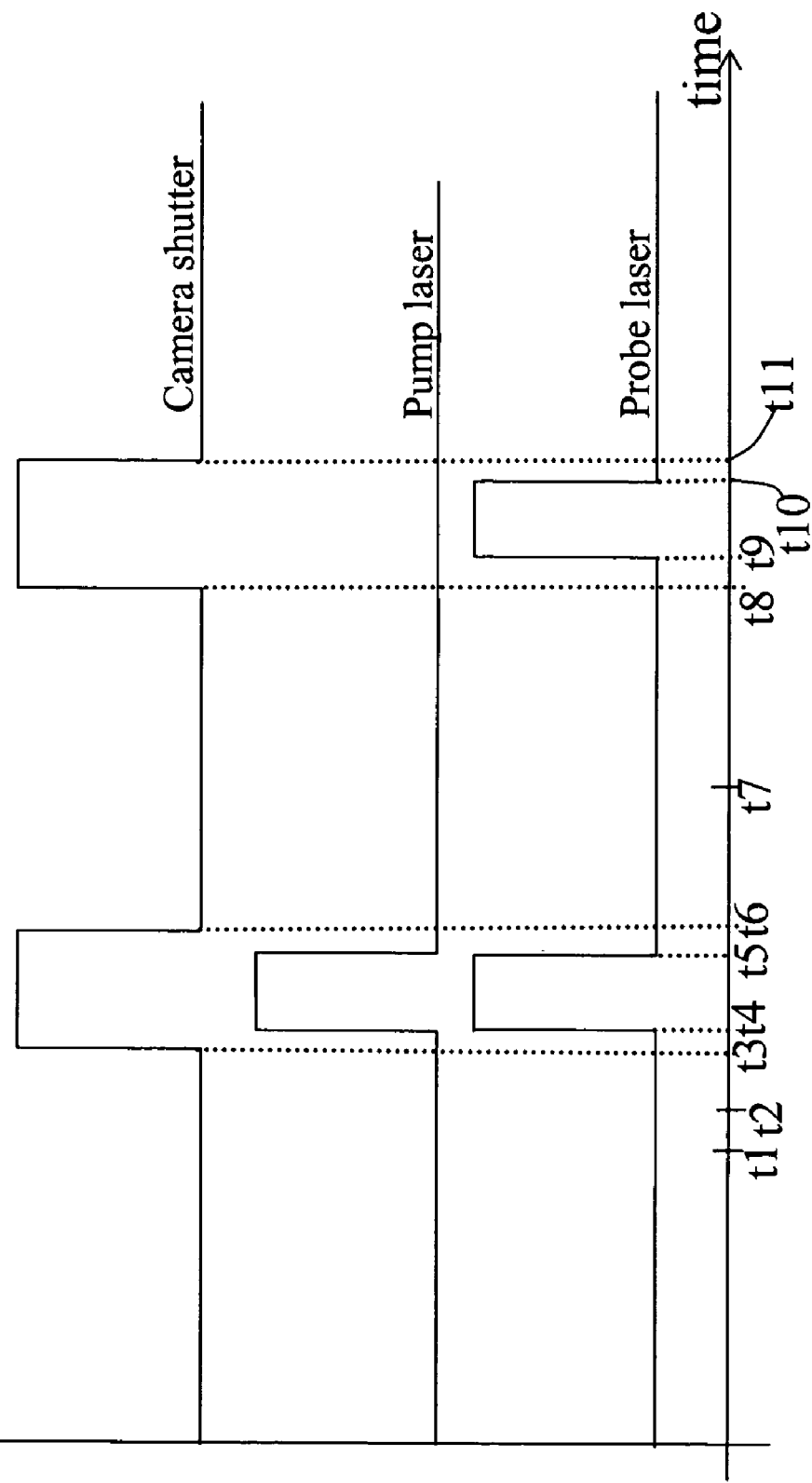

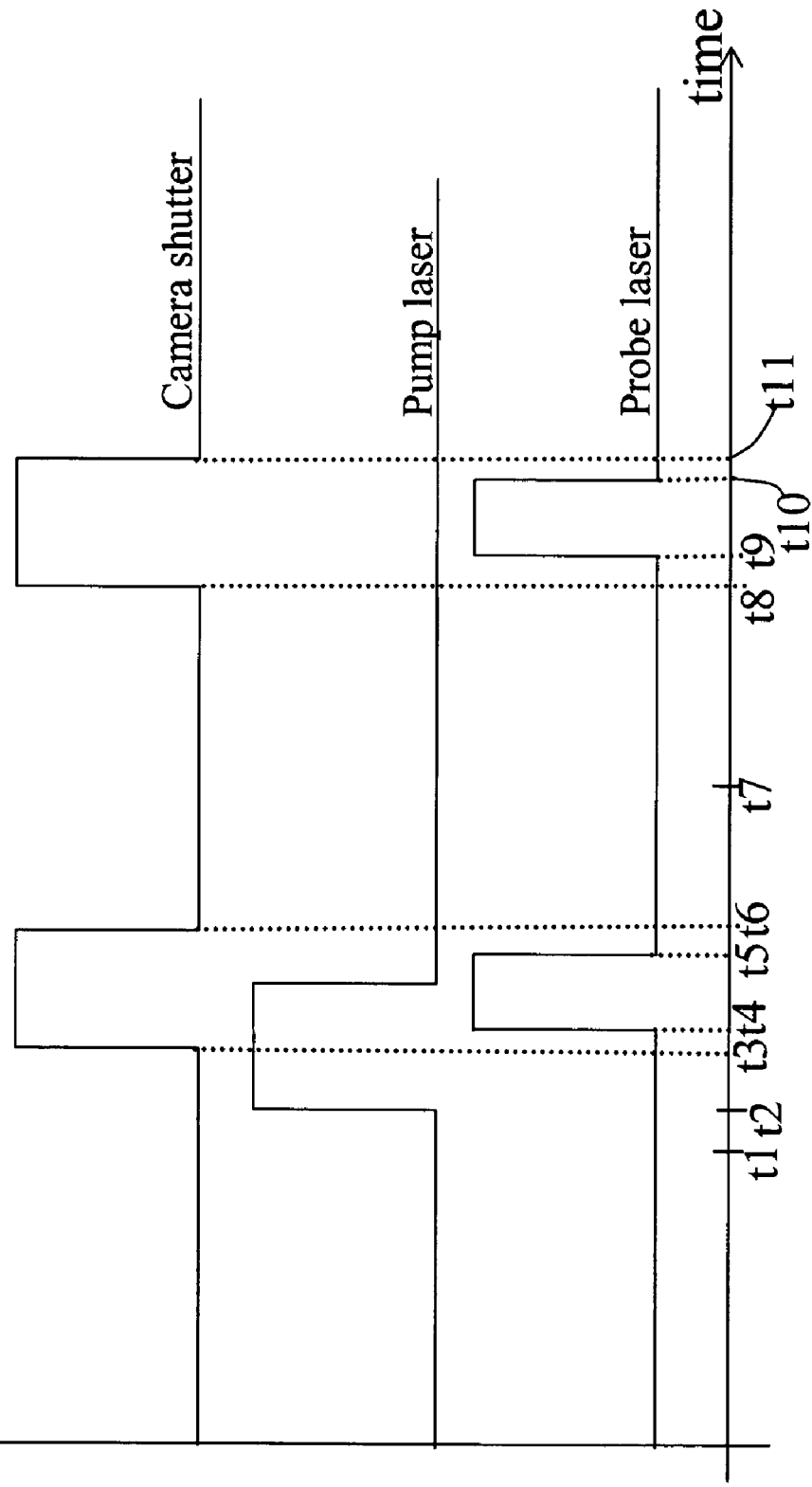

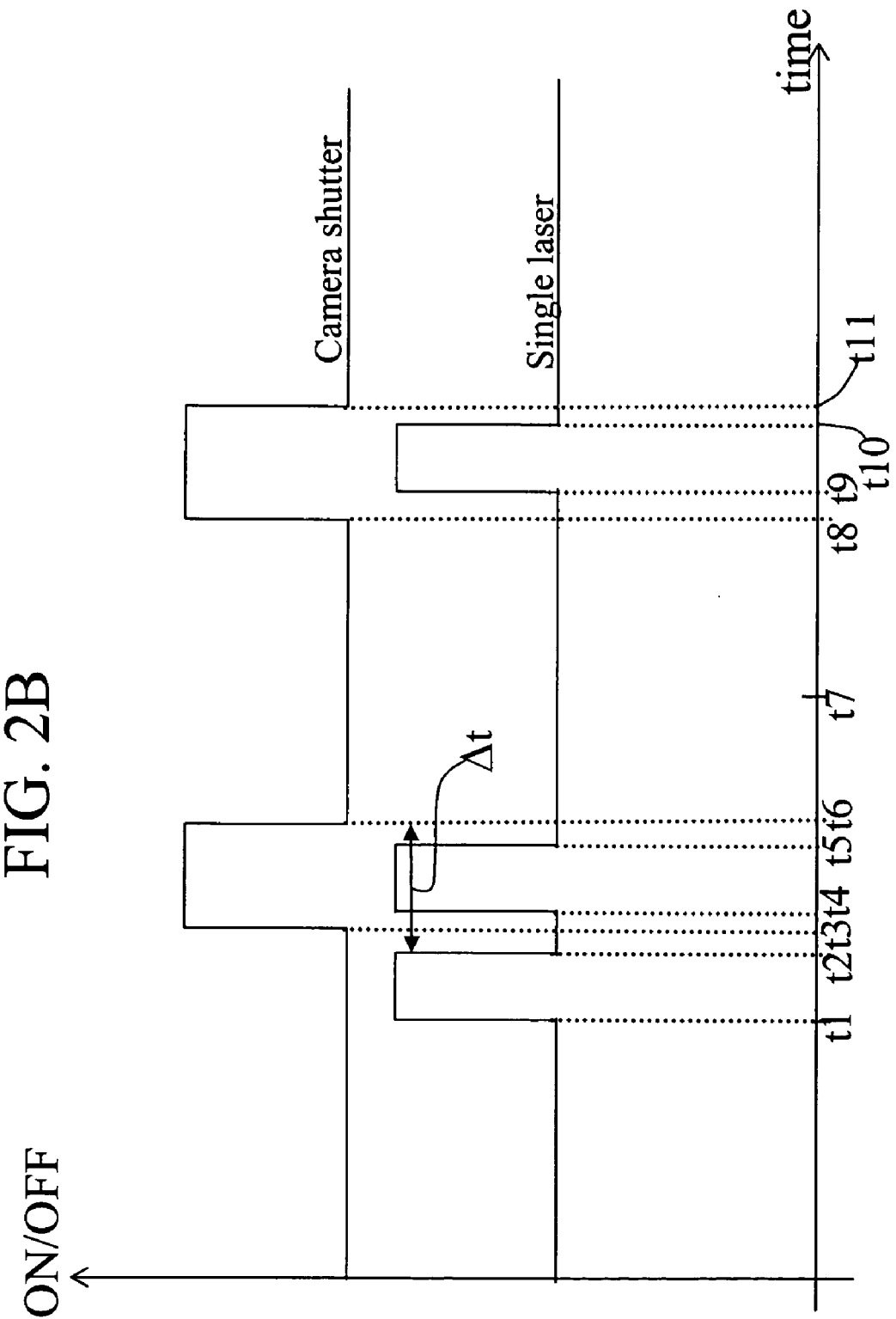

FULL FRAME THERMAL PUMP PROBE TECHNIQUE FOR DETECTING SUBSURFACE DEFECTS

CROSS-REFERENCE TO RELATED APPLICATIONS

This application claims the priority of U.S. Provisional Application No. 60/459,908 entitled "Full-frame thermal pump-probe technique for detecting subsurface defects" filed Apr. 1, 2003 by Daniel Some. U.S. Provisional Application No. 60/459,908 is incorporated by reference herein in its entirety.

This application incorporates by reference herein in its entirety, the commonly-owned and co-pending U.S. application Ser. No. 10/423,354 entitled "Optical Technique for Detecting Buried Defects in Opaque Films" filed Apr. 25, 2003 by Daniel Some, published on Nov. 6, 2003 as U.S. patent application Publication 2003206292A1.

This application incorporates by reference herein in its entirety, the commonly-owned and co-pending U.S. application Ser. No. 10/097,442 entitled "Multi-Detector Defect Detection System And A Method For Detecting Defects" filed Mar. 12, 2002 by Evgeni Levin et al., published on Sep. 18, 2003 as U.S. patent application Publication 20030174878 A1.

This application incorporates by reference herein in its entirety, the commonly-owned and co-pending U.S. application Ser. No. 10/200,580 entitled "Method For Detecting Defects" filed Jul. 23, 2002 by Evgeni Levin et al., published on May 29, 2003 as U.S. patent application Publication 20030099392 A1.

This application incorporates by reference herein in its entirety, the commonly-owned and concurrently filed U.S. Application No. 10/813,407 entitled "High Throughput Measurement Of Via Defects In Interconnects" filed by Jiping Li et al.

BACKGROUND

Semiconductor structures are inspected prior to, during, and after patterning procedures. Patterned metal films used in integrated circuit devices are often created using a damascene technique, in which a pattern is etched in an insulating dielectric layer, and subsequently filled using any of several standard deposition techniques, e.g., chemical vapor deposition (CVD), physical vapor deposition (PVD), or electrocopper plating (ECP). In the course of this process defects may be created inside or under the metal, such as voids, delamination, underfill or underetch of the dielectric, and other interface-related defects. Such buried defects are difficult to detect due to opacity of the surface layer.

U.S. Pat. No. 4,710,030 discloses use of a pump beam of short, non-destructive laser pulses (0.01–100 ps duration) to induce a thermo-elastic deformation, or stress waves, in a structure being tested, and to monitor the transient response of the structure using a low-power laser probe beam that is directed to the area of the deformation. By analyzing the intensity of the returning probe beam, information regarding defects and other characteristics of the structure can be inferred.

Besides reflections of short-pulse-induced stress waves, voids and interface defects are known to produce other physical effects in response to a pump beam, such as changes in acoustic dispersion properties, and reduced heat dissipation. These effects are discussed in an article entitled "Picosecond Ultrasonics" by Grahn et al., IEEE Journal of Quantum Electronics, Vol. 25 No. 12, pp. 2562–2568 (December 1989).

Moreover, U.S. Pat. No. 5,633,711 discloses monitoring a transient response to an excitation laser pulse that impinges on and locally heats a structure. In this disclosure, besides the intensity of the probe beam, phenomena such as acoustic oscillations and polarization disturbances are taken into account.

U.S. Pat. No. 6,320,666 discloses an intensity modulated pump laser beam, which is focused onto a sample so as to excite the sample periodically. Periodic heating by the pump beam creates a time varying deformation in the sample surface. A probe laser beam, obtained from a second laser, is focused onto the sample within the periodically heated area. A photodetector monitors the reflected power of the probe beam and generates an output signal responsively thereto. The output signal is filtered and processed to provide a measure of the modulated optical reflectivity of the sample.

U.S. Pat. No. 5,748,317 discloses the use of laser time-delayed pump and probe beams for determining the thermal properties of thin film. Measurements of reflectance and other optical characteristics are used to estimate the Kapitza resistance of a film. Inferences regarding the structure of the film or interfaces therein are made using reference data obtained from simulation or from another sample.

U.S. Pat. No. 6,253,621 discloses analysis of acoustic waves that are generated in a sample under test in response to a pulsed laser that is directed to a micro-spot on the sample and scanned. Acoustic waves are detected, and an acoustic index of refraction of a portion of the conductive structure is calculated as a function of the wave. The acoustic index of refraction is then spatially mapped over the sample.

U.S. Pat. No. 6,606,401 discloses detecting defects by comparing periodic structures, such as wafer dies. The signals for each wafer die are compared to at least the signals from the two nearest neighbor dies. Preferably the two wafer dies are located on either side of the die, in the same row as the die. See also U.S. Pat. No. 5,917,588 for a description of defect detection by analyzing a difference image among nearby reticle fields of a specimen wafer.

U.S. Pat. No. 5,131,755 discloses one configuration in which a substrate is compared to prestored expected characteristic features. Also disclosed is a second configuration in which first and second patterns in a region of the surface of at least one substrate are inspected by comparing one pattern against the other and noting where they agree with each other.

U.S. Pat. No. 6,297,879 discloses inspecting a photomask using a modified microscope, image comparison software and a CCD camera. The microscope is modified to view the photomask out of focus and at low magnifications. The image is compared with a reference image such as an image from another die or a database. Any discrepancies between images indicates a defect in the photomask.

U.S. Pat. No. 5,450,205 discloses measuring etching or deposition rate uniformity in situ using a CCD camera to view the wafer during plasma processing. The CCD camera records the temporal modulation of plasma emission or laser illumination reflected from the wafer; the modulation is caused by interferometry as thin films are etched or deposited. U.S. Pat. No. 5,450,205 also describes storing a time sequence of data signals corresponding to the signals generated by the CCD camera over a period of time. The storage is connected to data processing means for comparing the data signals for at least one sensing means of the array over a portion of the time period, and from comparisons determining the change of thickness of the film over the portion of the time period.

Each of the above-identified U.S. Patents is incorporated by reference herein in its entirety. Also incorporated by reference herein in its entirety is the above-identified article in IEEE Journal of Quantum Electronics.

SUMMARY

Several embodiments of the invention image an area of the substrate at least twice, once with and once without heating, to obtain two images that are respectively called hot image and cold image. Heat may be applied to the area being imaged in any manner, including use of a heating beam (also called "pump" beam). In many embodiments, the heat is applied in such a manner as to generate a thermal gradient at the top surface. Note that slowly heating the wafer through the bottom surface of the substrate is insufficient in most embodiments.

In such embodiments, the hot image is obtained while heat is dissipating from the area, whereas the cold image is obtained after at least a majority of heat has dissipated. The hot and cold images are compared with one another in most embodiments, and the comparison results are used to identify one or more areas that are suspected to have a subsurface defect.

In some embodiments, if the comparison result of an area differs significantly (e.g. by a predetermined value) relative to the results of comparison in other (e.g. surrounding) areas, then the area may be flagged as having a defect therein. In other embodiments, if the comparison result at an area exceeds a predetermined value for the area, then the area is deemed to have a defect. Either or both of the just-described predetermined values may be set to a different value for each area, depending on the type of material expected to be present at the area in the wafer that is being fabricated.

In several embodiments, the comparison results in numerous locations of an area together form a differential image, and a number of such differential images are obtained by repeatedly heating, imaging and comparing. The numerous differential images are averaged, to improve the signal to noise ratio. Moreover, signal to noise ratio may also be improved by adjusting the gain and/or offset of such images.

BRIEF DESCRIPTION OF THE DRAWINGS

FIGS. 1G and 1H illustrate, in timing diagrams, the relative times at which a pump laser, a probe laser and a camera shutter are turned on and off by embodiments that are different from the embodiments illustrated in FIG. 1D.

FIG. 2B illustrates, in a timing diagram, the relative times at which the single laser arid a camera shutter are turned on and off by embodiments of the type illustrated in FIG. 2A

FIG. 4 illustrates, in a block diagram, an alternative system for imaging hot and cold images in accordance with the invention wherein the heating beam is reflected by a beam splitter and the probe beam passes there-through.

DETAILED DESCRIPTION

Several embodiments of the invention image an area of a semiconductor wafer (also called "substrate") twice, a first time with heating by beam 111 (also called "pump" beam or "heating" beam), and a second time without heating by beam 111. The image obtained in the presence of heating is herein referred to as a "hot" image, and the image obtained without heating is herein referred to as a "cold" image. During the capture of these two images, another beam 141 (also called "probe" beam) illuminates the area to be imaged, and both images are captured (successively one after another) by a camera 160 that is sensitive to the wavelength of beam 141.

Figure 1A:
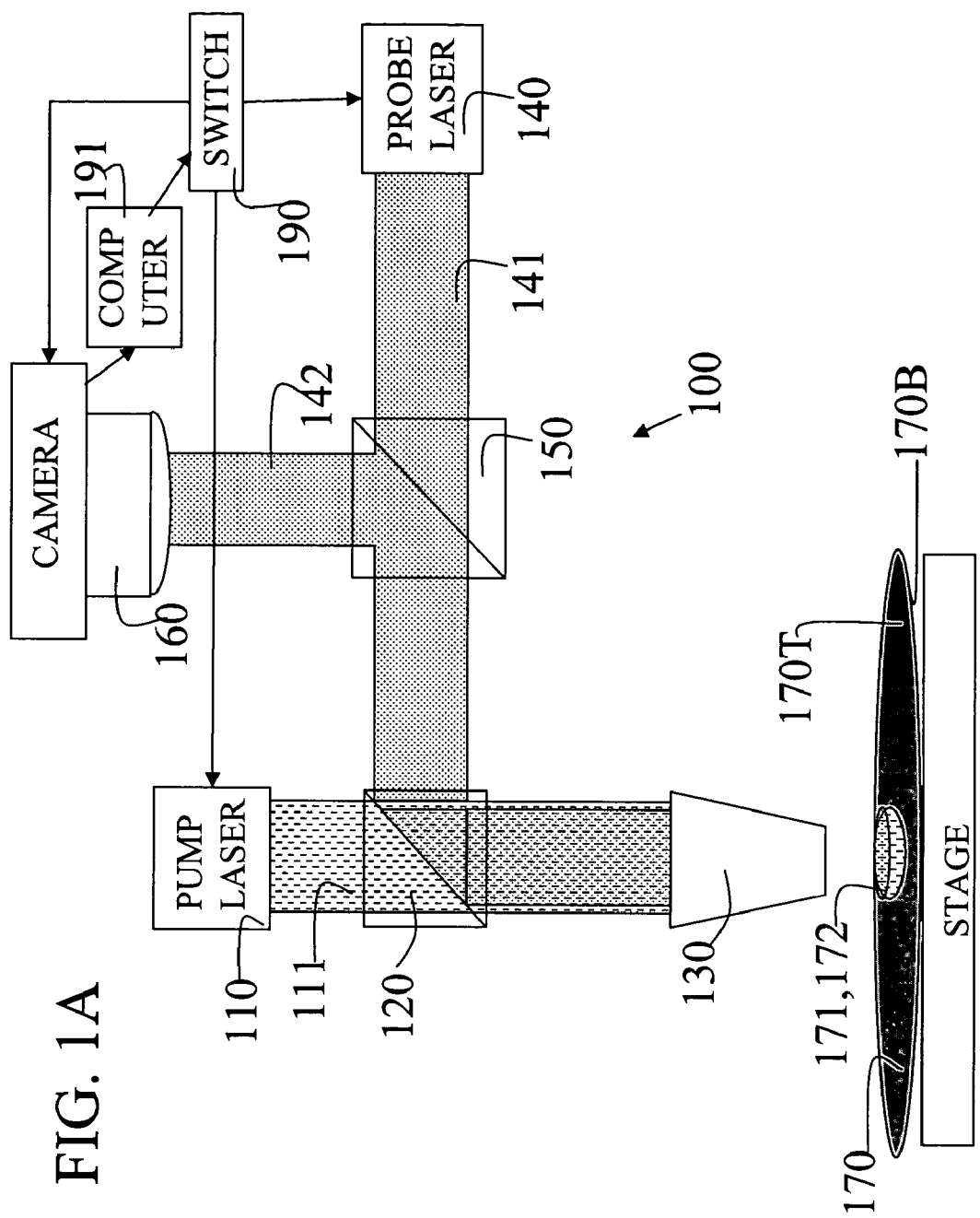
FIG. 1A illustrates, in a block diagram, a system for imaging hot and cold images and comparing them to identify a defect in some embodiments in accordance with the invention.
Figure 1B:
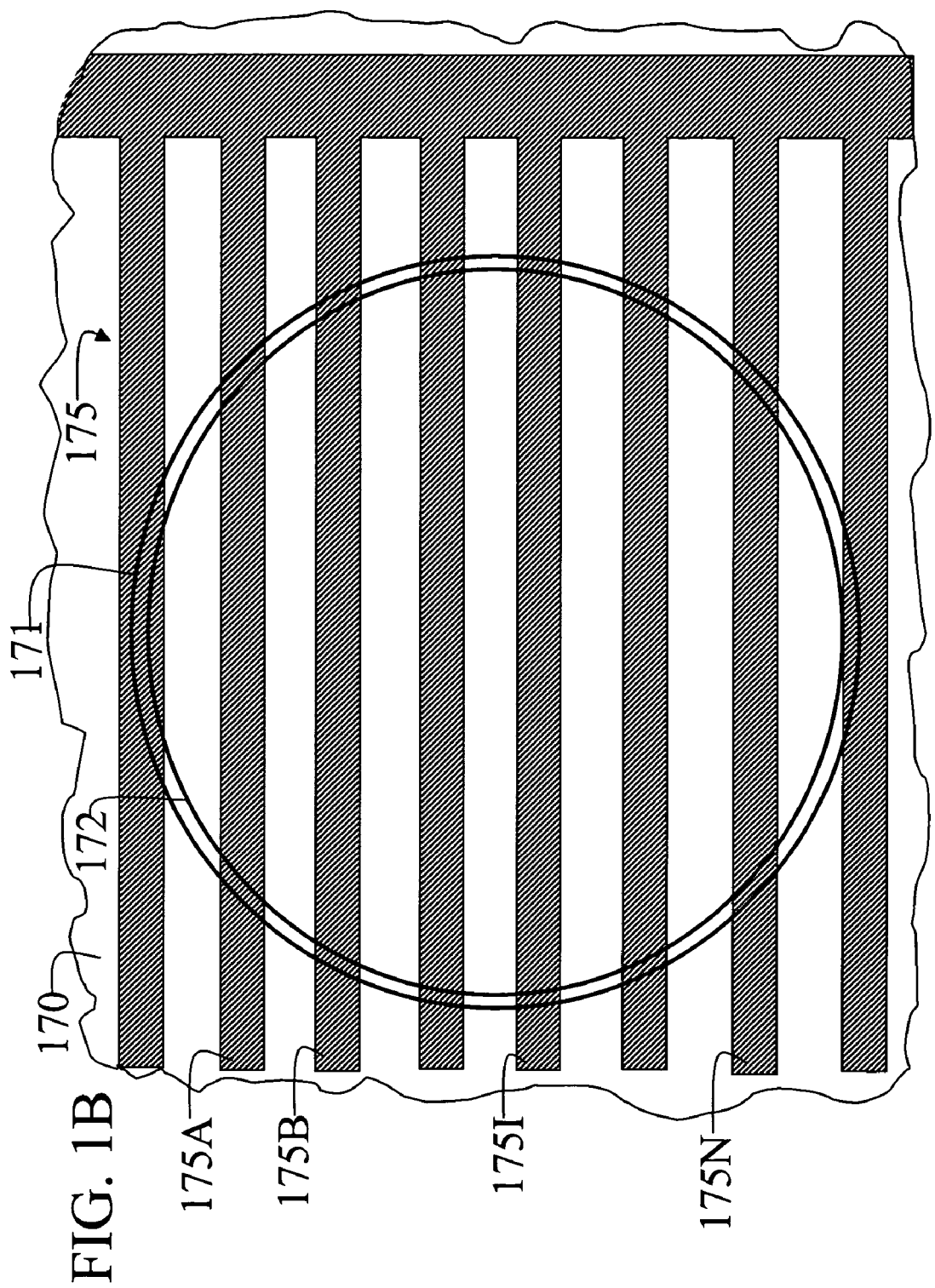
FIG. 1B illustrates, in an enlarged plan view, regions 171 and 172 on substrate 170 that are illuminated by embodiments of the type illustrated in FIG. 1A.

Camera 160 in FIG. 1A includes a two-dimensional array of sensors, such as a charge-coupled device (CCD) camera. In some embodiments, camera 160 has a number of sensors arranged in a square e.g. of sides 512×512 (i.e. over 25,000 sensors). Camera 160 can be, for example, non-interlaced progressive-scan CCD with image size of 640×480 pixels and speed of 120 frames per second (120 fps), such as Pulnix TM-6710. Depending on the optical magnification and the size of aperture of camera 160, regions 171 and 172 on substrate 170 that are illuminated by the respective beams 111 and 141 can be of sufficiently large diameter to cover an area containing a large number of the features to be evaluated. As illustrated in FIG. 1B, if a comb structure or a serpentine structure is being evaluated, regions 171 and 172 cover a number of conductive lines 175A–175N that are parallel to one another (wherein $A \leq I \leq N$, N being the total number of lines).

For example, if the diameter of region 172 is 500 microns, then such a camera 160 can capture in a single image the data from up to 250 conductive lines (e.g. 1 micron wide with 1 micron separation) with each line connected to a conductive layer underneath by 250 vias. Depending on the embodiment, a smaller area with fewer lines can imaged by such a camera, e.g. if greater resolution is desired.

For example, in a first embodiment, several tens of features are imaged, in a second embodiment hundreds of features are imaged, in a third embodiment thousands of features are imaged, and in a fourth embodiment tens of thousands of features are imaged. Regardless of the precise number of features that are imaged in a single frame by camera 160, it is to be understood that more than one such feature (e.g. via or line) is imaged in some embodiments of the invention. In such embodiments, a cell-to-cell comparison is carried out, for example by use of cell-to-cell defect detection algorithms which compare nominally identical cells which are spaced on a regular grid, facilitating comparisons within a single image. Note that other embodiments do not require multiple cells within an image, but instead compare images of nominally identical areas (which are centered at identical locations) in adjacent dies on the substrate. Specifically, as described below, averaged differential images from two corresponding areas in two dies of a substrate under evaluation are compared in some embodiments, and an area having a significant difference in intensities is deemed to be defective. A difference in intensities, to be considered "significant" in such a method 180, depends on the specific application, and is preset (e.g. by trial and error).

Some embodiments of the invention perform method 180 (FIG. 1C) to find a defect in substrate 170. Specifically, in act 181, an area to be evaluated is identified to the system, e.g. by a human operator. The identified area may contain a test structure in some embodiments, e.g. between two adjacent die in substrate 170 although a test structure is not used in alternative embodiments In embodiments that use the test structure, the test structure may take any form, such as a serpentine, a comb or a via chain. In alternative embodiments, the identified area may contain a functional structure which is a normal part of circuitry being fabricated in the die (i.e. not a test structure). Regardless of whether a test structure or a functional structure is contained in the identified area, in act 182, the identified area is heated and photographed to obtain a "hot" image. Specifically, the image is obtained by simultaneously making a number of measurements in the identified area (e.g. by using an array of sensors), to obtain a corresponding number of pixels for the image.

Heat may be applied in any manner in act 182, although in some embodiments of the type illustrated in FIG. 1A, a heating beam 111 is used. Note that the term "top surface" refers to an exposed surface 170T (FIG. 1A) of substrate 170 that is closest to the active regions therein whereas the bottom surface 170B is the surface that has no active regions. The bottom surface 170B normally faces and is in contact with a stage on which substrate 170 is supported during evaluation. In act 182, the heat is applied such that a rapidly switchable thermal gradient is produced at the top surface of substrate 170. Note that applying heat to bottom surface 170B of the substrate is likely to be unsatisfactory, if such a process takes too long to heat and cool the massive substrate. For example, thermally conductive paths from bottom surface 170B of substrate to the top surface 170T may not exist or even when existent may not be evenly distributed.

Heating beam 111 may be produced by a laser 110 which can be, for example, a AlGaAs diode laser that emits electromagnetic radiation of wavelength 830 nm. Note that in alternative embodiments, heating beam 111 may be produced by an incoherent source, e.g. arc lamp (and modulation of heating beam 111 is achieved, for example, by pulsing or chopping with a mechanical chopper wheel). In addition, system 100 creates probe beam 141 by use of another laser 140 that can be, for example, InGaAs diode laser that emits electromagnetic radiation of wavelength 1480 nm. Many embodiments use a frequency doubled Nd:YAG laser at 532 nm wavelength to generate probe beam 141. In some embodiments, the two beams 111 and 141 are preselected to have sufficiently different wavelengths to enable a dichroic beam splitter to distinguish therebetween (e.g. have a contrast ratio of more than 10000:1). Note that the beam splitter need not have 10,000:1 contrast ratio—because this is merely the overall contrast ratio that is achieved in many embodiments. In embodiments where the beam splitter has a lower contrast ratio, spectral filters are added into the optical path of such embodiments to achieve the just-described high contrast ratio. Heating beam 111 (generated by laser 110) has a power of, for example, 10 milliwatts/micron$^2$ whereas probe beam 141 has several orders of magnitude lower power of, e.g. 100 microwatts/micron$^2$.

Another embodiment uses continuous wave (CW) lasers as heating laser 110 and probe laser 140. For example, Coherent Verdi DPSS (diode pumped solid state) CW laser producing 532 nm can be used as probe laser 140. Alternatively, a source of non-coherent light can be used to produce the heating beam 111. The specific mechanism used in modulation of heating laser 110 depends on the embodiment. For example, in some embodiments, heating laser 110 is implemented as a diode laser, and laser 110 is directly modulated, by modulating the electrical current used to drive laser 110 with a suitable alternating current power supply. As another example, in another embodiment, heating laser 110 is implemented as a CW laser, and a mechanical chopper or other device (such as acousto-optic crystal or electro-optic crystal) is used to implement modulation.

A hot image is captured in accordance with the invention by camera 160 while heat is dissipating from the area, and this can happen either when beam 111 is still illuminating the area or shortly thereafter. For example, FIG. 1D illustrates a time period t1–t2 during which period the pump laser (or other heating source) is on. A short while thereafter at time t3 the camera shutter is opened. Data is collected by camera 160 to form the hot image during a time period between t3 and t6. Note that most embodiments capture an image produced by probe beam 141 after it is turned on at time t4, although the camera 160 was turned on earlier at time t3. The hot image is formed in camera 160 during the time probe beam remains on, i.e. between times t4 and t5.

The time period t4–t5 is selected to ensure that the hot image is formed while heat that is applied to the area during time period t1–t2 is still dissipating from the area. Heat dissipation during period t1–t2 follows the profile of heat application during this time (and if heat is applied at a constant rate then heat also dissipates at the steady rate). The temperature of the heated area drops off exponentially after time t2 when heating beam 111 is turned off. Specifically, heat dissipation causes the temperature of the sample to decay in an exponential fashion, which can be approximated by the equation $$T(t)=T_0 e^{-at},$$

wherein T is temperature, $T_0$ is initial temperature, t is time, and "a" is a decay constant. The presence of various defects, such as voids and interface defects, generally slows the dissipation process, decreasing the value of the decay constant a. Assuming that the reflectivity or surface deformation is proportional to the temperature, a significant change in the decay constant a is indicative of the presence of a defect.

Therefore, the duration Δt (between times t2 and t6 in FIG. 1D) is selected to be sufficiently small to ensure that a temperature rise due to presence of heat from beam 111 is noticeable in the hot image. In some embodiments, duration Δt is selected to be the time at which the temperature after time t2 falls to (1/e) of the steady state value during period t1–t2. In other embodiments, duration Δt is selected experimentally, after trial and error with different durations, to find subsurface defects as described next. In some embodiments, duration Δt is on the order of a few microseconds (e.g. 2–3 microseconds).

Figure 1C:
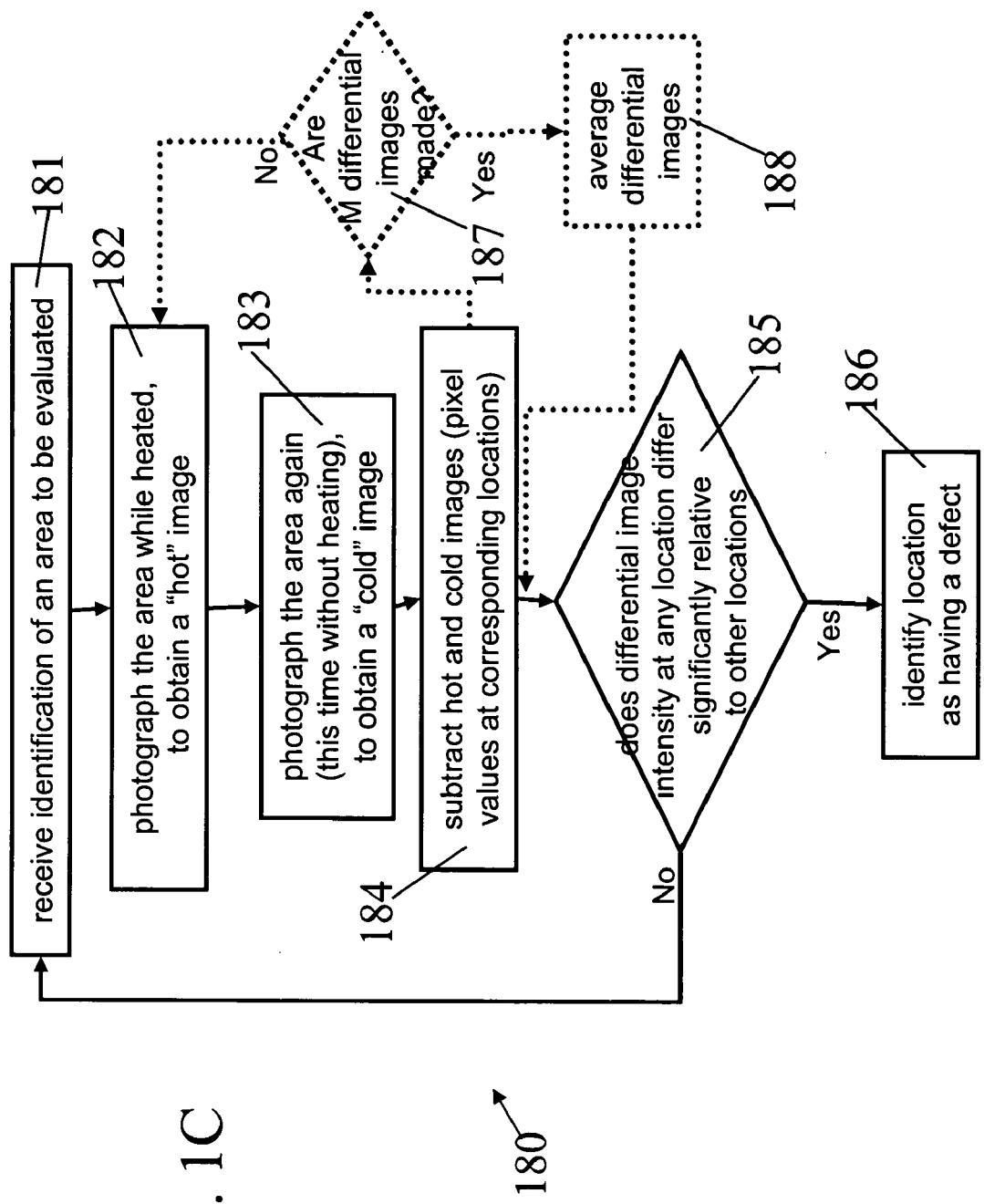
FIG. 1C illustrates, in a flow chart, acts performed by embodiments of the type illustrated in FIG. 1A.
Figure 1D:
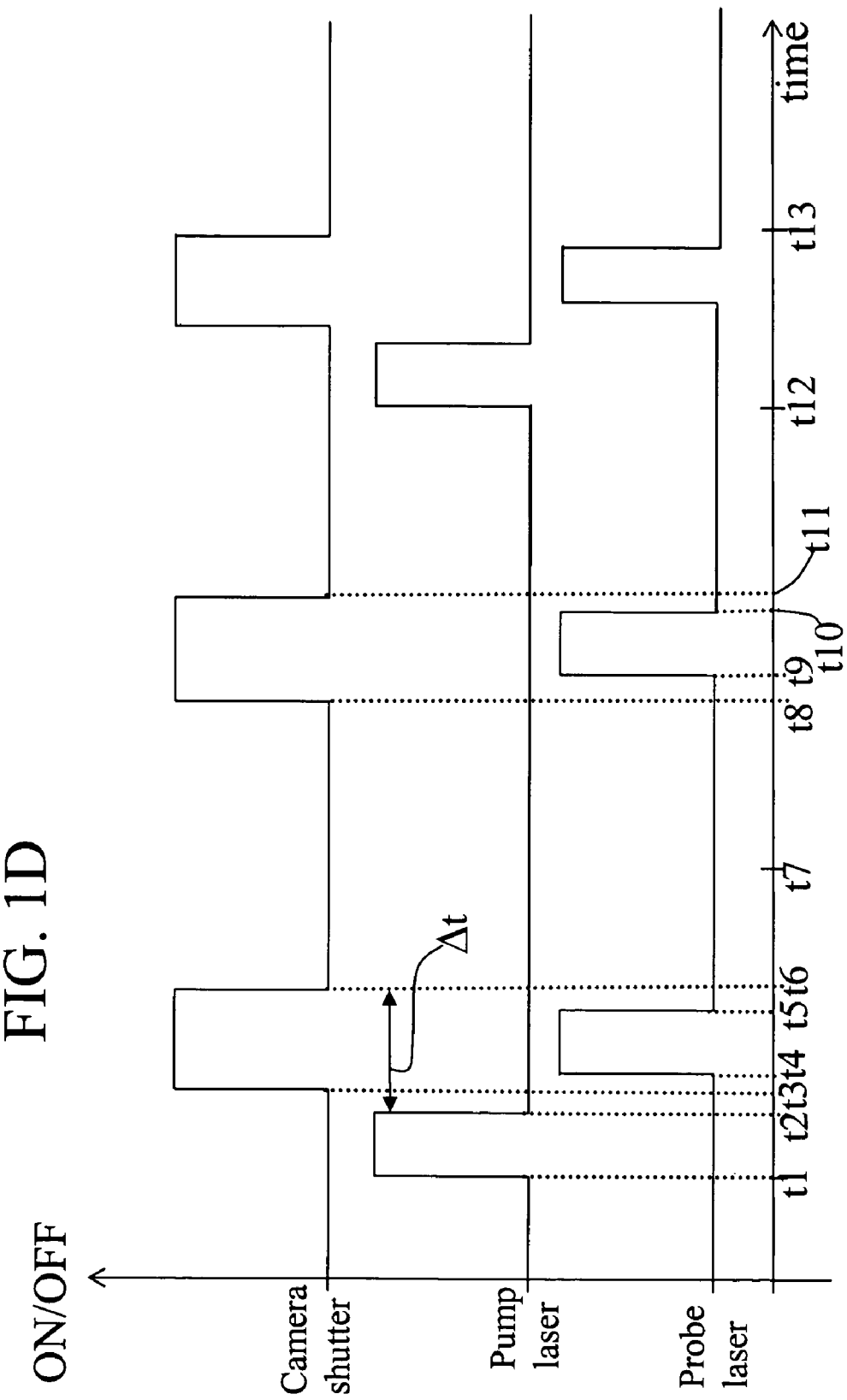
FIG. 1D illustrates, in a timing diagram, the relative times at which a pump laser, a probe laser and a camera shutter are turned on and off by embodiments of the type illustrated in FIG. 1A

After passage of a predetermined time delay (which may be selected as discussed in paragraph above and paragraph below) e.g. at time t7, camera 160 is turned on again during time period t8–t11 to capture another image as per act 183 (FIG. 1C). Hence, in act 183, a "cold" image is captured, of the same area that was imaged in act 182. Referring to FIG. 1D, to assist camera 160 in image capture, probe beam 141 is shone again on this area during period t9–t10 (which falls within period t8–t11), but note that pump beam 111 is not turned on during this time. For this reason, the image being captured is considered "cold." As noted above (in case of the "hot" image), at this stage as well, most embodiments capture an image that is produced specifically by use of the probe beam (i.e. not an image with just ambient light or thermal emission).

In several of the just-described embodiments, act 183 (FIG. 1C) which captures the cold image is performed after all (or almost all) heat from beam 111 has dissipated from the illuminated area, e.g. after steady state conditions are reached (at time t7 in the example of FIG. 1D). However other embodiments do not wait to capture the cold image until after steady state conditions are reached. Instead, such other embodiments may wait only until a majority (i.e. more than 50%) of the heat applied by beam 111 has dissipated from the illuminated area.

As noted above, due to exponential decay in the rate of heat dissipation, the heated area may take a very long time to reach steady state conditions. For this reason, a cold image may be captured in some embodiments, even while a minority (i.e. less than 50% e.g. 25%) of the heat applied by beam 111 is still dissipating from the illuminated area. Note that the signal to noise ratio (SNR) is improved in embodiments where the amount of applied heat that has not yet dissipated during capture of the cold image, preferably less than 10% of the heat deposited by the pump beam.

In several embodiments, as described elsewhere herein, the signal to noise ratio is improved by repeatedly capturing a hot image and a cold image successively one after another. In such embodiments, after capture of a cold image at time t11, the above-described acts for capture of a hot image between times t1 and t6 are repeated between times t12 and t13 (FIG. 1D). For this reason, the pump beam is turned on again at time t12, followed by the acts of the type described above. After capture of the hot image between times t12 and t13, the above-described acts for capture of a cold image between times t8 and t11 are repeated (not shown in FIG. 1D). In this manner, the acts performed between times t1 and t11 may be repeated any number of times, to obtain an alternating series of hot and cold images (e.g. hot image 1, cold image 1, hot image 2, cold image 2, hot image 3, cold image 3 . . . ).

In some embodiments, timing relationships for switching on and off pump laser 110, probe laser 140, and camera 160 of the type illustrated in FIG. 1D and described above are implemented by a switching circuit 190 that is electrically connected to each of these items, as shown in FIG. 1A.

Specifically, in certain embodiments switching circuit 190 automatically turns on and off probe laser 140 and camera 160 at a common frequency, e.g. 100 hertz. Moreover, switching circuit 190 of such embodiments also automatically turns on (and off) pump laser 110 at half of the just-described common frequency, e.g. at 50 hertz. In several embodiments, switching circuit 190 turns on and off items 110, 140 and 160 by supplying power thereto in a timely manner as described herein (and switching circuit 190 receives power from a power supply which is not shown). However, in other embodiments, one or more of items 110, 140 and 160 may be individually responsive to a control signal for turning on and off, in which case switching circuit 190 supplies control signal(s) in the same timely manner.

Switching circuit 190 of such embodiments also implements a first phase difference between generation of the pump beam 111 and a first generation of the probe beam 141 immediately thereafter (i.e. the time period t1–t4 illustrated in FIG. 1D). The first phase difference is kept sufficiently small to ensure that sensors in camera 160 capture a hot image of the area while heat is dissipating therefrom. Switching circuit 190 of these embodiments also implements a second phase difference between generation of the pump beam 111 and a second generation of the probe beam 141 immediately after the first generation (i.e. the time period t1–t9 also illustrated in FIG. 1D). The second phase difference is kept sufficiently large to ensure that sensors in camera 160 capture a cold image of the area, after a majority of heat applied by beam 111 is dissipated therefrom.

The just-described switching circuit 190 may be implemented in any manner apparent to the skilled artisan in view of the disclosure. For example, a "discrete" embodiment of circuit 190 uses an oscillator at the common frequency, and delay elements coupled to the oscillator to implement the timing relationships for turning on and off the probe laser 140 and camera 160. Furthermore, a frequency divider is driven by the oscillator and is used to turn on and off the pump laser 110. Note that an explicit discrete component implementation of the switching circuit is not a critical aspect of this invention.

Some embodiments use computer control with standard programmable timers, such as a dedicated timing board, e.g. the National Instruments 6601 Counter/Timer as switch 190. Specifically, this board generates control signals that are supplied to each of the laser(s) and the camera. In some embodiments, this board is inserted into a slot in the chassis of computer 191, and is programmed by computer 191. Computer 191 provides the timing definitions at which each of the laser(s) and the camera is to be turned on/off by this board.

Camera 160 of some embodiments includes a frame grabber which supplies each image (immediately after capture) to a computer 191 (FIG. 1A). Hence at (or shortly after) time t6 (FIG. 1D) computer 191 receives a hot image 192 (FIG. 1E), and at (or shortly after) time t11 (FIG. 1D) computer 191 receives a cold image 193. Note that the conductive lines have a different reflectivity in hot image 192 than in cold image 193 because the reflectivity (and hence visibility) of the conductive lines is changed in the hot image due to higher temperature from application of heat (because reflectivity changes with temperature). Computer 191 of some embodiments contains a processor that is programmed in accordance with the invention to compare images 192 and 193, e.g. via a comparator 195 which may be implemented by subtracting one image from another image in an arithmetic logic unit (ALU), e.g. to implement act 184 (FIG. 1C). Images 192 and 193 have corresponding regions 192X and 193X of intensities that are not noticeably different from intensities in similar surrounding regions (e.g. the intensity in regions 192X and 193X falls below a threshold for identifying a defect). The results of subtracting the pixel values in images 192 and 193 at each of several locations within an area yield the pixels of a differential image 194. Differential image 194 has a region 194X of noticeably greater intensity (e.g. the intensity is greater than the threshold) which is indicative of a defect (that was not noticeable in the individual images 192 and 193).

Differential image 194 represents the thermal behavior of the sample because the subtraction operation eliminates the fixed reflectivity image and retains only that portion that has changed due to changing temperature. Differences in intensities at any specific location in differential image 194 are compared in some embodiments to other locations (e.g. in surrounding areas) by use of any of numerous inspection algorithms, e.g. by use of a computer programmed with such algorithms. Examples of automatic comparison algorithms for defect detection are described in U.S. patent application Ser. Nos. 10/097,442 and 10/423,354 and 10/002,221 each of which has been incorporated by reference above.

One such algorithm (multiple perspective algorithm) supports, among others, the possibility of using the hot image to decide which areas are conducting and therefore of interest in further evaluation (e.g. metal surfaces with higher reflectivity are of greater interest for void detection than a dielectric surface). Such automated inspection of some embodiments includes die-to-die comparison, wherein identical regions in adjacent dies are imaged and results of imaging (e.g. averaged differential images therefrom) compared.

In some embodiments, a ratio of the difference image to the cold image is used in comparison (so as to normalize out local reflectivity differences). For example, several embodiments use the ratio of the difference to the cold image, to compensate for local reflectivity differences due to surface properties (roughness, etc). As another example, certain embodiments use a product of the difference image with the cold image, to compensate for reflectivity differences due to variations in width of the conductive regions (if the line is wider, the overall reflectivity will be higher, but the thermal conductivity and thermal capacity will also be higher so the temperature change will be lower and thus the reflectivity difference lower).

As yet another example, various embodiments use related mathematical operations on the difference image designed to compensate for local changes in reflectivity unrelated to the presence of defects, as would be apparent to one skilled in the art. These operations may depend on the specific optical configuration implemented in the embodiment.

Typically in an automated inspection procedure, the regions to be imaged are decided upon at the outset of evaluation of a substrate. However, in some embodiments an iterative process (described below) is used with a human operator. If the field-of-view does not cover a desired region, then the substrate is translated to subsequent adjacent positions and imaged so as to cover the entire region (e.g. in a die). Note that some embodiments ensure that adjacent regions being imaged (within a given die) have at least a slight overlap.

Hence, in alternative embodiments, a human operator views image 194 to check (as per act 185 in FIG. 1C) if the intensity at any location in differential image 194 differs significantly from the corresponding intensity at other locations in image 194. In one alternative embodiment, the human operator only compares an image intensity at a location of a conductive line with image intensities at adjacent locations in the same conductive line, or in an adjacent conductive line.

Typically, if there is a defect, an intensity of the differential image 194 at the location of the defect becomes significantly higher or lower than image intensities at other locations, depending on the embodiment. If such a significant difference is found, then a defective location is identified as per act 186. On the other hand, if the image intensities along the locations of conductive lines are substantially uniform, then the human operator may conclude that there is no defect, in which case the system returns to act 181 (discussed above).

At this stage another area on the same wafer (e.g. adjacent to the area just evaluated) may be identified by the human operator for evaluation (e.g. if a test structure spans across both the just-described areas). For example, an area covered by a test structure may be divided into four quadrants, and each quadrant is evaluated in the above-described manner. Alternatively an area centered at an identical location in another die in the wafer may be so identified in act 181, and then evaluated in the above-described manner.

Figure 1E:
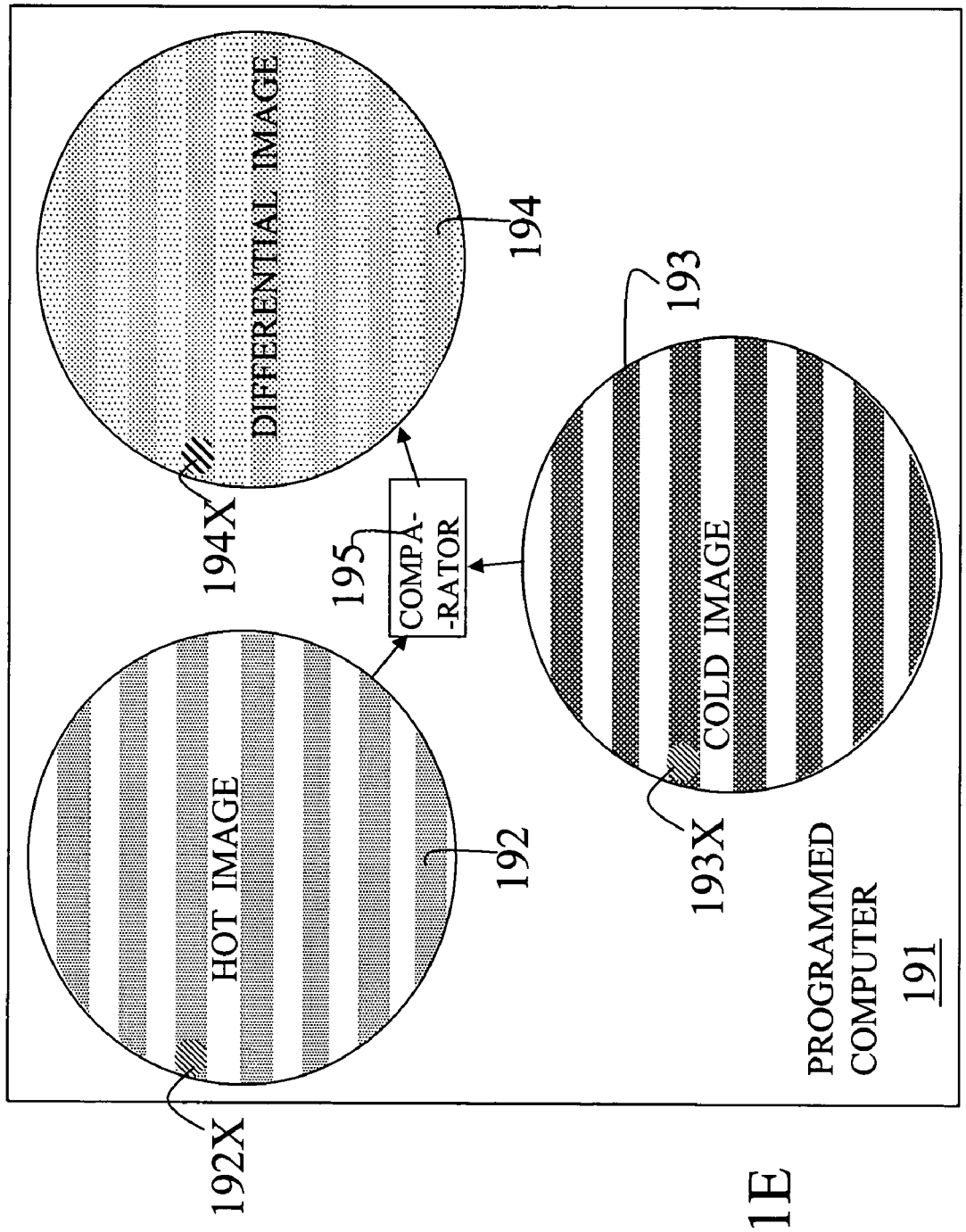
FIG. 1E illustrates, in a block diagram, a computer programmed to compare a hot image and a cold image to obtain a differential image in several embodiments of the invention.

In some embodiments wherein the signal to noise ratio (SNR) is low in differential image 194, the SNR is improved by averaging image 194 over a number of repetitions of acts 182–184, as illustrated by acts 187 and 188 in FIG. 1E. Specifically, in such embodiments, after act 184 is performed, an act 187 is performed to check if M subtractions have been made (i.e. if M differential images have been created). If so then a differential image 194A is averaged (see act 188 in FIG. 1E) with other differential images 194B–194M (FIG. 1F) of the same area.

The other differential images 194B–194M of the same area are obtained by repeated performance of acts 182 and 183 (in the same area in the same die) to obtain additional hot and cold images (e.g. starting at time t11 in FIG. 1F), and repeated performance of act 184 to obtain each differential image 194J for each pair of hot and cold images. Note that the data being averaged in act 188 is not the raw data of a number of hot images or cold images or both. Instead, it is the intensity difference between a hot image and a cold image that is being averaged in act 188. Averaging the intensity differences improves the signal to noise ratio.

Figure 1F:
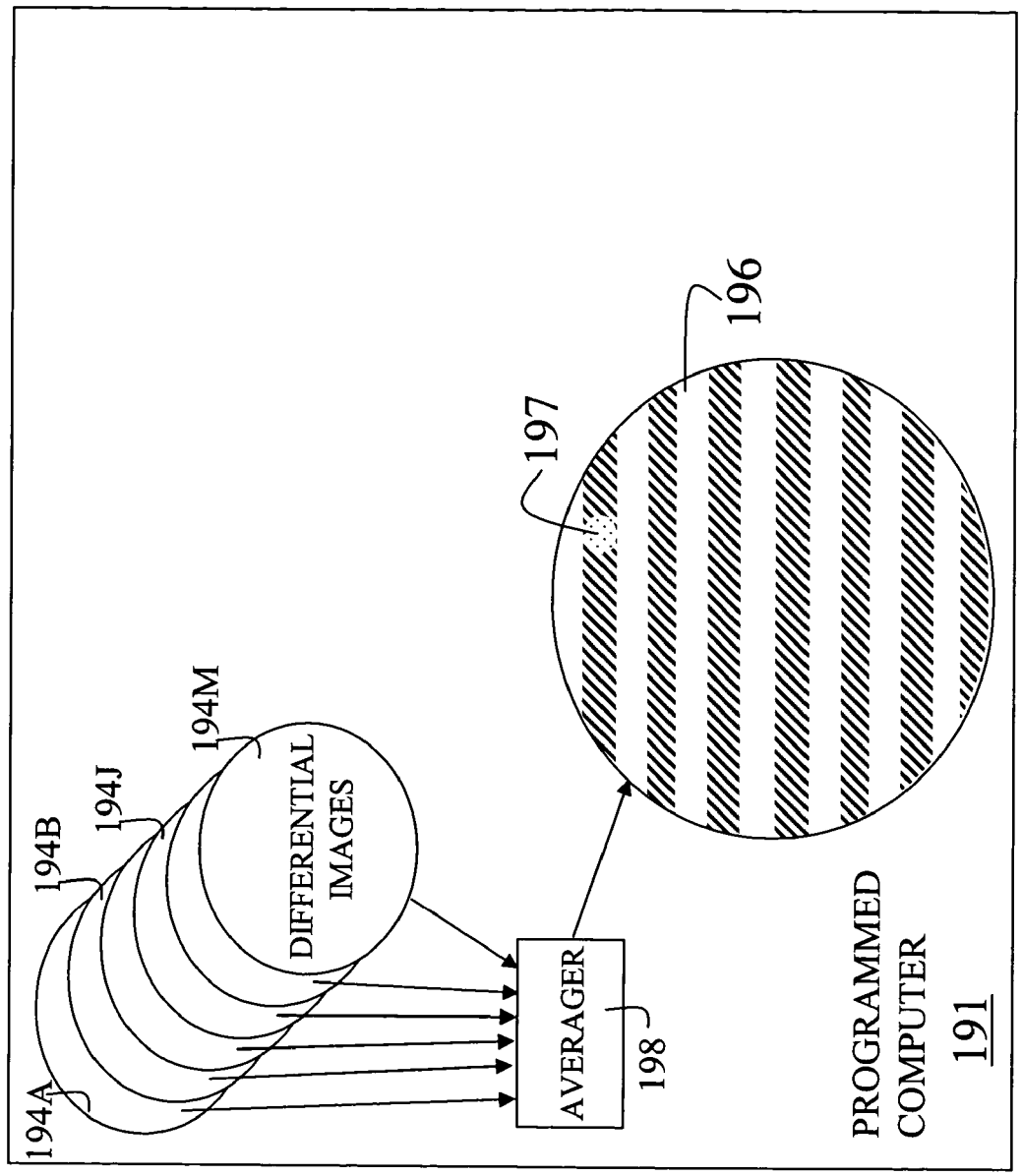
FIG. 1F illustrates, in a block diagram, the computer of FIG. 1E further programmed in some embodiments of the invention to average a number of differential images to create an averaged differential image whereby the signal-to-noise ratio is improved and a defect becomes visible.

Note that in FIG. 1F, $A \leq J \leq M$ and M is the total number of differential images 194A–194M that are averaged by computer 191. The value of M depends on the embodiment, and may be determined experimentally by trial and error. In several embodiments, M is on the order of 100, although M as high as 1000 may be used in some embodiments and M as low as 10 may be used in other embodiments. Note that the precise value of M to be used in any embodiment may be picked based on the signal to noise ratio (SNR) of the system. For example, a system that uses a CCD camera 160 with a large well (capacitor) has a higher SNR inherent in each differential image, and therefore requires a smaller M than a camera 160 with a smaller well. As noted above, such a CCD camera 160 may have 512×512 sensors. Moreover, a value of 100,000 electrons in a well is typical, for a CCD camera 160 but too low for a single measurement in many embodiments of the type described herein (because shot noise on 100,000 electrons is 330 electrons, or 3×10-3, which can easily be larger than the expected reflectivity difference). With such a CCD camera 160, if at least 100 frames are integrated, just a single measurement requires 1 second (assuming 100 fps). In several embodiments, the CCD camera 160 has wells with a million electrons, and only 10 frames are integrated, thereby to obtain a measurement of the same SNR as the just-described other embodiments but within $1/10^{th}$ the time.

In such embodiments, computer 191 is programmed to implement an averager 198, and it is the averaged differential image 196 generated by averager 198 that is used in act 185 (discussed above). Averager 198 may be implemented by an arithmetic logic unit (ALU) as noted above. Also as noted above, the averaged differential image 196 has a better SNR than any single differential image, and in such a case a defect 197 becomes visible.

In addition to lasers 110 and 140, camera 160 and switching circuit 190 that are described above, system 100 (FIG. 1A) includes three optical devices. Specifically, a dichroic beam splitter 120 is located in a path (also called "pump" path) between laser 110 and substrate 170, and an objective lens 130 is also located in this pump path, adjacent to substrate 170. Objective lens 130 can be, for example, a 0.9 NA, 100× objective lens available from Nikon of Yokohama, Japan. Opposite to the dichroic beam splitter 120 and laterally separated therefrom is another beam splitter 150 through which passes the probe beam 141 from laser 140 in the direction of incidence (towards substrate 170).

Figure 4:
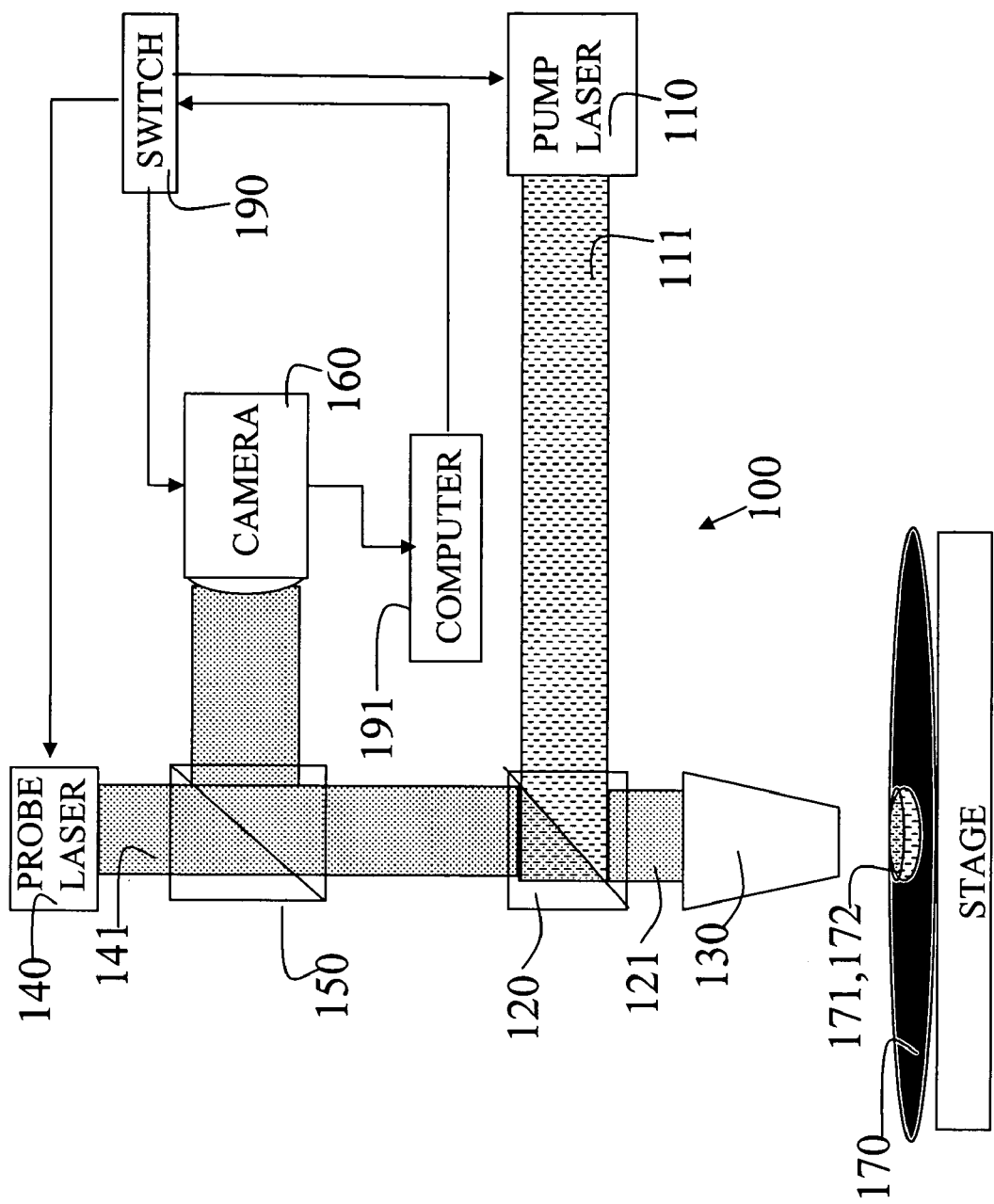

Dichroic beam splitter 120 can be, for example, LLC SWP-45-RS810-TS532-PW-1025-C available from CVI Laser, which reflects >99.5% of heating beam 111 of 810 nm wavelength while transmitting >90% of probe beam 141 of wavelength 532 nm. In this example, an additional shortwave-pass filter (not shown) is used in front of the camera 160 (e.g. CVI SPFS-650-1.00) to remove any residual pump beam signal e.g. the remaining 0.5%. Note that the just-described exemplary embodiment deviates from FIG. 1A as follows: the pump beam 111 is reflected by beam splitter 120 and the probe beam 141 is transmitted through beam splitter 120. Such a configuration is illustrated in FIG. 4. Note that in many such embodiments, beam splitter 150 may be either non-polarizing beam splitter, e.g. CVI NCBS-532-100 (50/50 beam splitter), or polarizing beam splitter with a quarter wave plate (such as CVI PBS-532-100+CVI QWPO-532-10-4-R15). Embodiments that use polarizing beam splitter with a quarter wave plate require a polarized laser beam source as described in the next paragraph.

Note that a portion of probe beam 141 that is reflected by substrate 170 travels along the pump path (opposite to the incidence direction of pump beam 111) up to dichroic beam splitter 120. The reflected portion of the probe beam then travels from beam splitter 120 to beam splitter 150 and therefrom to camera 160 (and in this last leg the probe beam portion is identified as beam 142 in FIG. 1A). Note that beam splitter 150 is implemented in one embodiment by a polarizing beam splitter (PBS) and a quarter wave plate (QWP). Beam splitter 150 In this embodiment, simply pass through the probe beam 141 along the direction of incidence from laser 140 but reflects to camera 160 the probe beam from the opposite direction (i.e. from beam splitter 120). In this embodiment, the probe beam 141 from laser 140 is polarized, so as to be operative with the PBS. Note that pump beam 111 may or may not be polarized, depending on the embodiment.

Although in some embodiments, pump laser 110 is turned on during the period t1–t2 (FIG. 1D) which precedes the period t3–t6 during which time camera 160 is capturing the hot image, in several embodiments pump laser 110 is turned on and off simultaneous with capture of the hot image. Specifically, as illustrated in FIG. 1G, probe laser 140 is turned on during the period t4–t5 to enable camera 160 to capture the hot image, and in the alternative embodiments pump laser 110 is also turned on during this same period t4–t5. Note that any reflection of the pump beam 111 by substrate 170 is prevented from reaching camera 160 by dichroic beam splitter 120 (FIG. 1A). In such embodiments, an additional band pass filter (not shown) may be placed in the return path at camera 160, to remove any residual pump beam signal.

Note that in other embodiments, as illustrated in FIG. 1H, the period during which pump laser 110 is on only partially overlaps a period during which camera 160 captures the hot image. Specifically, in FIG. 1H, pump laser 110 is turned on at time t2 and is turned off between times t4 and t5. Numerous such embodiments with different timing relationships between when lasers 110, 140 and camera 160 are on will be apparent to the skilled artisan in view of this disclosure. In all such embodiments, an area illuminated by probe beam 141 is dissipating heat applied by heating beam 111 while camera 160 is capturing a hot image.

Figure 2A:
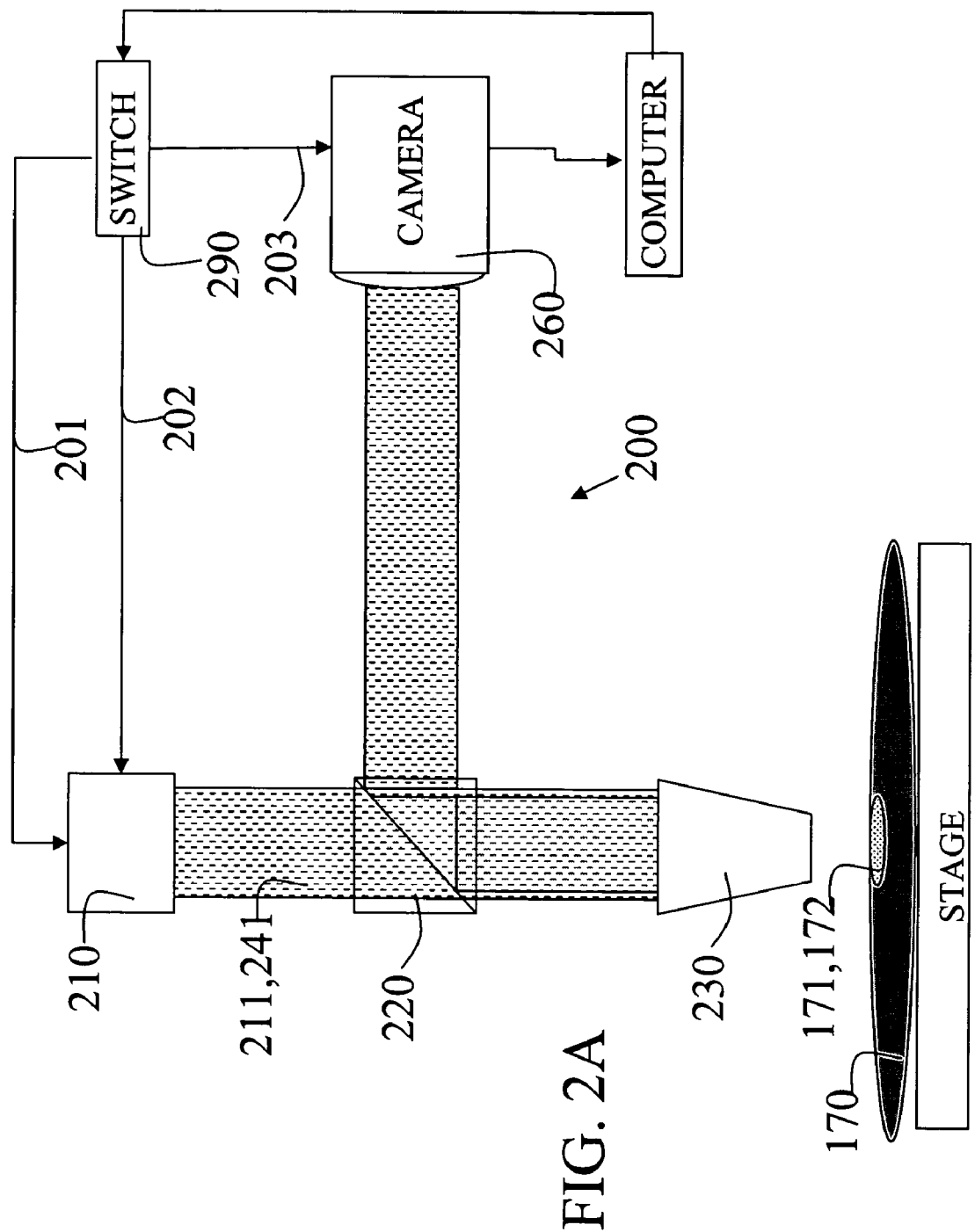
FIG. 2A illustrates, in a block diagram, a system of the type illustrated in FIG. 1A but using a single laser beam as both a probe beam and a pump beam in some embodiments in accordance with the invention.

In some alternative embodiments, system 200 (FIG. 2A) is similar or identical to system 100 (FIG. 1A) except for certain differences which are described next. Reference numerals in FIG. 2A are derived from the corresponding reference numerals in FIG. 1A by adding 100. System 200 uses only one laser 210 which is operable at two different intensities. The intensity of single laser 210 can be reduced, e.g. from a maximum intensity, by use of a variable attenuator, or alternatively in case of a diode laser the power supplied thereto is reduced.

When operated at a first (e.g. maximum) intensity, laser 210 forms a heating beam 211 and when operated at a second (e.g. lower) intensity, laser 210 forms a probe beam 241. Switch 290 controls the operation of laser 210 to generate either one of beams 211 and 241 (but not both). Switch 290 also operates camera 260 to form a hot image and a cold image, as illustrated in FIG. 2B. Note that system 200 has fewer components than system 100 and is therefore less expensive (e.g. because only one laser is used). However, system 200 requires laser 210 to have a small latency, so that it can be switched off and on very rapidly, e.g. between times t2 and t4 (FIG. 2B) as described next.

Specifically, switch 290 turns on the single laser 210 at the first intensity, thereby to heat substrate 170 between times t1 and t2 (FIG. 2B). Specifically, between times t1 and t2, switch 290 drives an active signal on line 201 and drives an inactive signal on line 202. At the end of the heating period, at time t2, switch 290 drives an inactive signal on both lines 201 and 202. Now, after laser 210 is turned off at the first intensity, at time t3 switch 290 drives an active signal on line 203 which in turn opens a shutter of camera 260. Camera 260 is now ready to form a hot image of the type described herein.

Next, during the period t4–t5, while camera 260 has the shutter open, switch 290 drives an active signal on line 202 and drives an inactive signal on line 201 thereby to turn on the single laser 210 at the second intensity, thereby to illuminate substrate 170 for imaging. At time t5, switch 290 drives an inactive signal on both lines 201 and 202. At time t6, switch 290 drives an inactive signal on line 203 thereby to close the shutter of camera 260. At this stage, the hot image is captured in camera 260 which supplies this image to a computer in the above-described manner.

Next, at time t7 steady state conditions are reached, and thereafter (in this particular embodiment) starting at time t8, switch 290 operates in a manner similar to the time period starting at time t3 (described above). Specifically, at time t8, switch 290 drives an active signal on line 203 which in turn opens a shutter of camera 260. Camera 260 is now ready to form a cold image. Next, during the period t9–t10, while camera 260 has the shutter open, switch 290 drives an active signal on line 202 and drives an inactive signal on line 201 thereby to turn on the single laser 210 at the second intensity, thereby to illuminate substrate 170 for imaging. At time t10, switch 290 drives an inactive signal on both lines 201 and 202 thereby to shut off laser 210. At time t11, switch 290 drives an inactive signal on line 203 thereby to close the shutter of camera 260. At this stage the cold image is captured in camera 260 which supplies this image to a computer in the above-described manner.

Figure 3A:
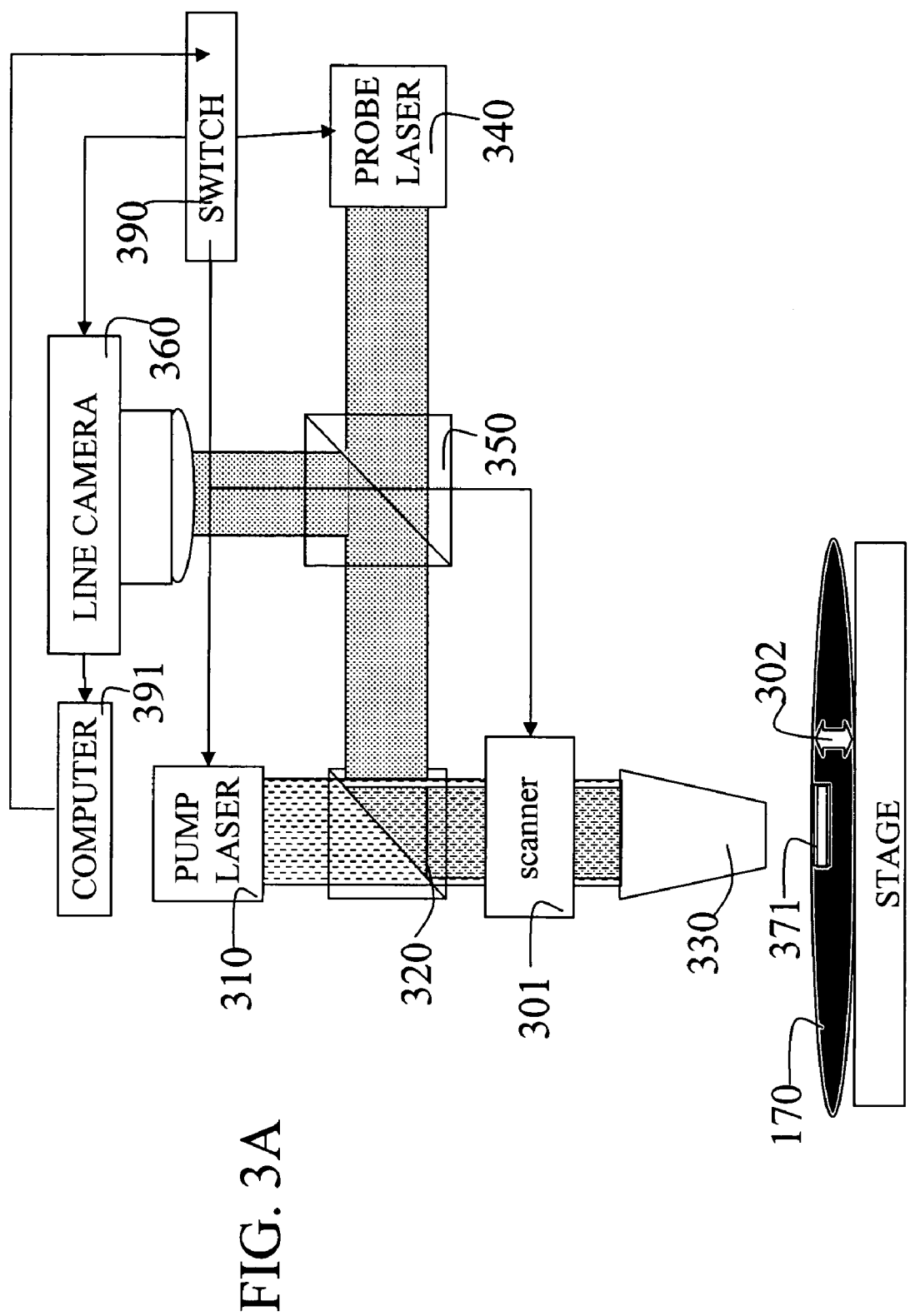
FIG. 3A illustrates, in a block diagram, a system of the type illustrated in FIG. 1A but using a line camera and a scanner that scans in a direction perpendicular to the length of the line camera.

In some alternative embodiments, system 300 (FIG. 3A) is similar or identical to system 100 (FIG. 1A) except for certain differences which are described next. Reference numerals in FIG. 3A are derived from the corresponding reference numerals in FIG. 1A by adding 200. System 300 uses a line camera 360, which contains a single line of sensors (i.e. 512 photodetectors (such as photo-diodes or photo-transistors) arranged along a straight line). In some embodiments, line camera 360 is capable of imaging a line of width on the order of 1–2 microns. Line CCD camera 360 can be, for example, DVL2098K manufactured by Lord Ingenerie of Corbreuse, France, 2098 pixels, line rate 9500/sec, variable electronic shutter, 16 bit digital output with 1 bit noise.

In system 300, pump laser 310 and probe laser 340 are similar to the corresponding lasers of system 100, except that pump laser 310 has a pulse width less than 1 $\mu$sec and the energy imparted in a pulse is on the order of 100 nJ. Probe laser 340 also has a pulse width less than 1 $\mu$sec and the energy imparted in a pulse is on the order of 10 nJ.

Moreover, system 300 includes a cylindrical lens 330 in a path of a combined beam formed by pump and probe beams 311 and 341, located immediately after dichroic beam splitter 320 instead of an objective lens. A similar lens (not shown) images the line of reflected probe beam 341 onto the line camera 360. Note that in most embodiments, homogenization of intensity is not an issue for both 2d (two-dimensional) and 1d systems of the type being described herein. If homogenization becomes an issue in an embodiment, it is solved for 2d systems by use of Newport Corp's GBS (gaussian beam shaper) refractive beam shaper which converts a Gaussian laser beam into a collimated flat-top beam with nearly 100% efficiency. A similar design is implemented for a 1d systems.

Furthermore, system 300 also includes a scanner 301 which is capable of scanning the laser lines over the test site (e.g. galvanometric scanning mirror). Alternatively the wafer itself may be scanned (by the stage), relative to the optical elements in system 300.

Figure 3B:
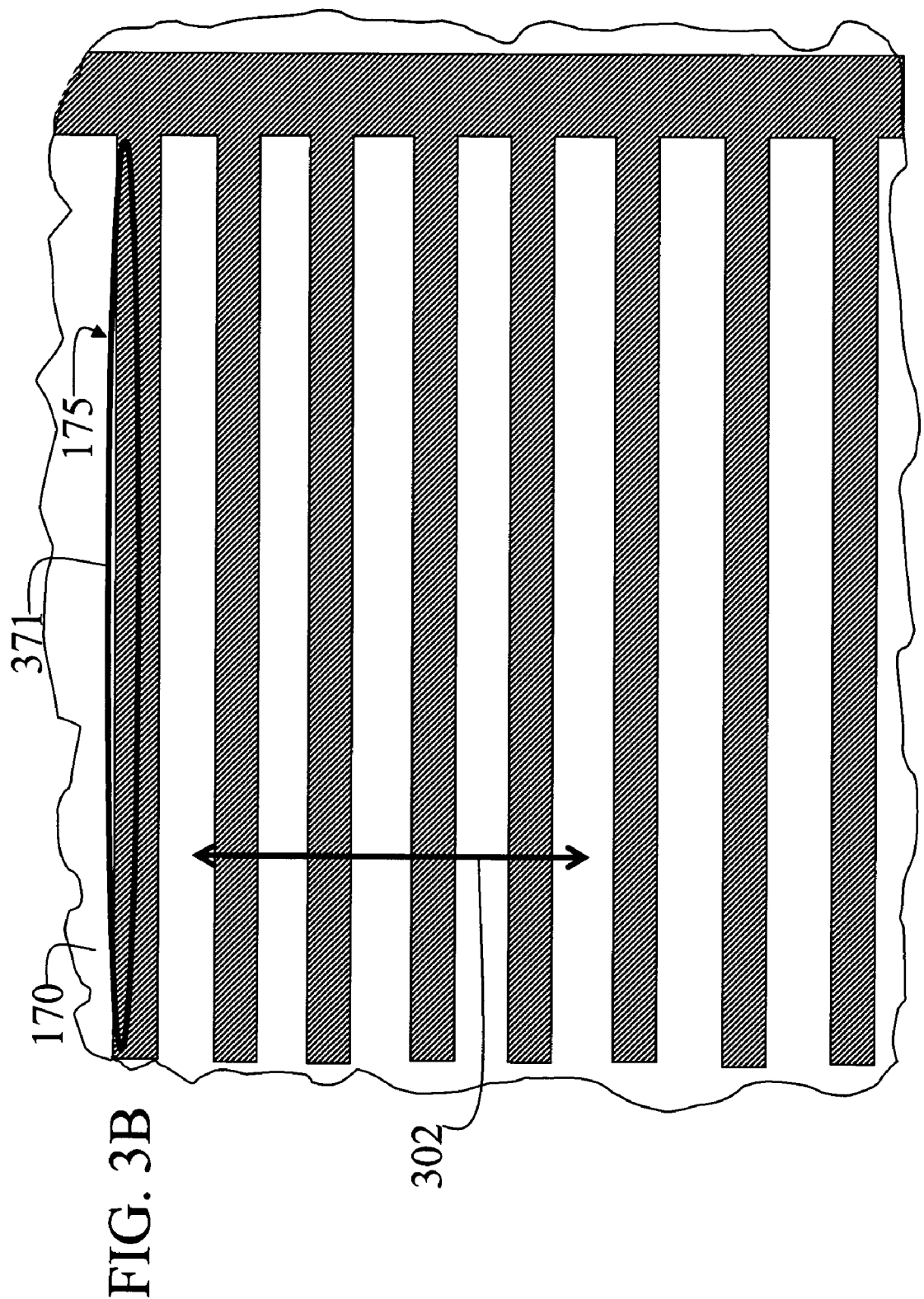
FIGS. 3B and 3C illustrate, in an enlarged plan view, relative positions of longitudinal region 371 and 372 respectively formed on substrate 170 by some embodiments of the type illustrated in FIG. 3A, at two different times during a scan.
Figure 3C:
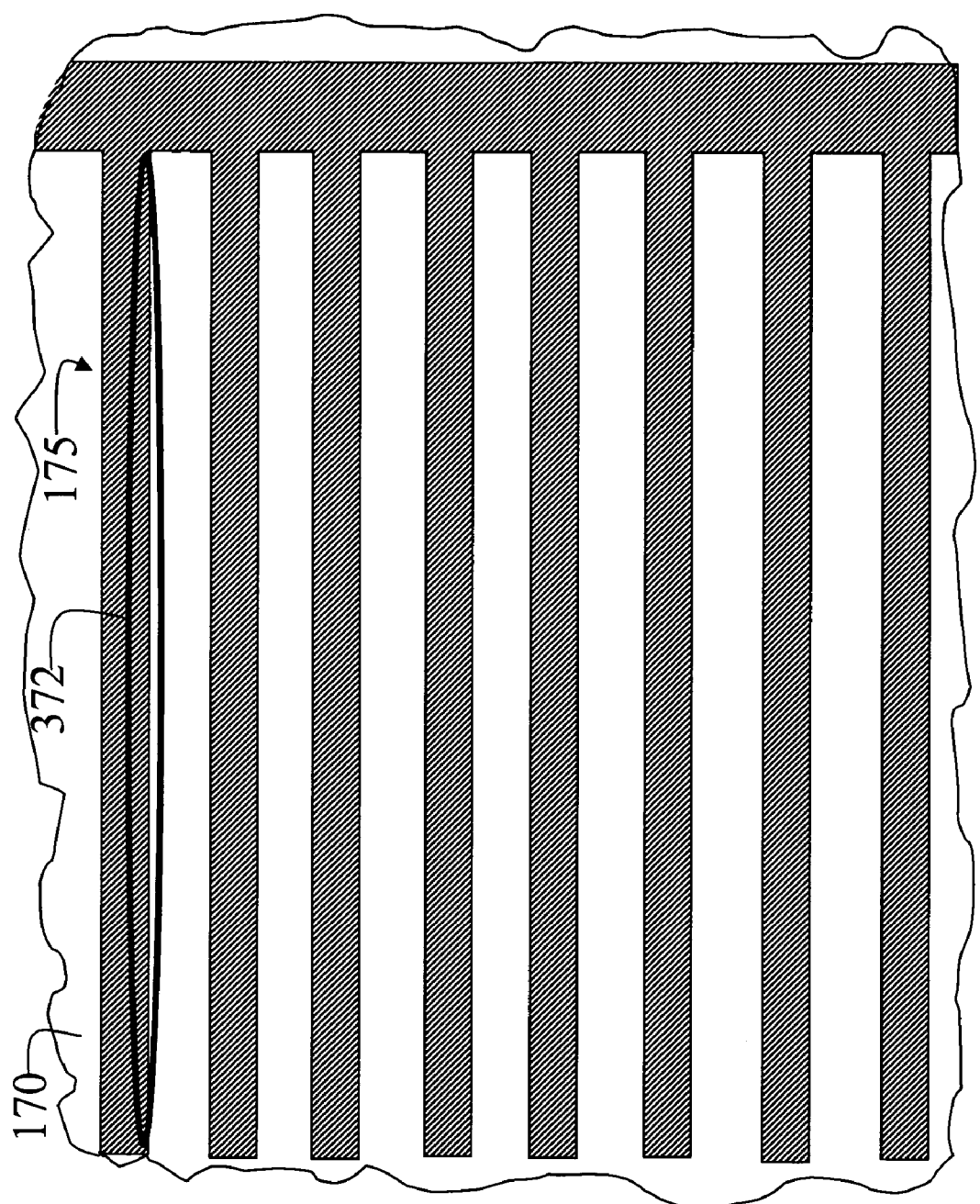

In such embodiments, a "hot" line image and a "cold" line image are both formed by a portion of the probe beam reflected by longitudinal region 371 (FIGS. 3A and 3B) on wafer 170. Note that a single region 371 is shown in FIG. 3A for convenience, as being the area illuminated by both the pump beam as well as the probe beam. A frame grabber in the line camera 360 supplies each line image to computer 391 as and when the image is formed. After an initial pair of hot and cold images are formed, and additional pairs of hot and cold images are obtained (by repetition), system 300 and wafer 170 are scanned relative to one another (either or both may be scanned) e.g. in a direction 302 which is perpendicular to a longitudinal axis of region 371, so that a new region 372 (FIG. 3C) is imaged in the next set of hot and cold images.

In several embodiments, pump laser 310 is timed about 5–20 $\mu$sec prior to start of the first probe beam pulse at time t4, and one frame before the second probe beam pulse at time t9. Scanner 301 of these embodiments is configured to scan slowly enough in order to acquire the necessary number of hot and cold images from each illuminated area. In embodiments that use a galvanometric scanning mirror as scanner 301, the mirror is positioned at each longitudinal region (e.g. region 371 in FIG. 3B), and kept stationary at that spot until M pairs of hot and cold images are acquired, before moving to the next longitudinal region (e.g. region 372 in FIG. 3C). Note that in some embodiments, continuous motion is not used and instead, the system moves in fixed steps. However, in alternative embodiments, the system and/or wafer are continuously moved relative to one another. In such alternative embodiments, the relative motion is kept slow enough to obtain the necessary number of images for integration from each pixel. In some embodiments, successive longitudinal regions being illuminated are made to overlap one another by about ¾, and so it doesn't matter if there are smaller increments there-between obtained by continuous movement.

In embodiments of the type illustrated in FIG. 3A, the switch 390 is coupled to scanner 301, to synchronize the timing therein. Such a switch 390 may contain, for example, any timing device well known in the art, such as National Instruments 6601 Counter/Timer. As noted above, such a timing device is operated under computer control, and the discrete component implementation of such a circuit is not a critical aspect of the invention.

A line scan system 300 of the type described above is sensitive to horizontal shorts or breaks (e.g. in a plane parallel to the surface of substrate 170), if such defects occur in the direction of scan. In contrast, system 100 of the type described above is not sensitive to such defects due to formation of a uniform two-dimensional pump illumination profile wherein there is little or no thermal gradient induced parallel to the surface of the conducting material, but a vertical thermal gradient is produced into the depth of the conducting material. For this reason, system 100 is useful for identifying defects in vertical paths from the surface of the substrate to locations in the depth in the substrate. In contrast, defects in a horizontal plane (e.g. a short between adjacent conductive lines or a break in a conductive line) can be detected by system 300 either in the above-described scan, or in another scan in a direction perpendicular thereto after rotating the system by 90 degrees relative to the substrate. Some embodiments of this type improve the sensitivity of system 300 to lateral defects by imposing a spatial delay between the pump and probe as well as a time delay, in order to detect lateral heat gradients.

Comparison of a hot image with a cold image as described above in reference to act 184 (FIG. 1C) can be implemented by programmed computer 191 in any manner apparent to the skilled artisan in view of this disclosure. For example, in some embodiments, the intensities in a cold image are simply subtracted from corresponding intensities in a hot image, at every one of several locations in the area being imaged, thereby to obtain a differential image.

In other embodiments, during the comparison in act 184, computer 191 is programmed to adjust intensities in the hot image to ensure that a majority of adjusted intensities are at least substantially same as (e.g. within 10% of) intensities at corresponding locations in the cold image. For example, an offset is computed by averaging all image intensities in the hot image and subtracting the resulting average from a corresponding average of all image intensities in the cold image. Also, a gain is computed by subtracting the minimum intensity in the hot image from the maximum intensity in the hot image, and dividing the resulting range by a corresponding range of image intensities in the cold image. In some embodiments, offset and gain are calculated by performing a least-squares fit of the pixels $H(i,j)=A*C(i,j)+B$, where $H(i,j)$ and $C(i,j)$ are the corresponding pixel values of the hot and cold images at the location (i,j), B is the offset and A the gain. Note that (i,j) are indices in x and y directions.

Next, the offset and gain are used to adjust the intensities of one of the images, e.g. the hot image's intensities are adjusted by subtracting the offset and dividing by the gain. After such adjustment, depending on the structure being imaged and the signal to noise ratio of the system, in some embodiments a majority of (e.g. greater than 50% of) adjusted intensities in the hot image become substantially same as (e.g. within 10% or even 1% of) intensities at corresponding locations in the cold image. Specifically, in many embodiments, almost all of the adjusted intensities match (because a defect, if present, is only a small part of the image).

Note that although adjustment of the intensities in the hot image has been described above, such adjustment can be alternatively performed on the intensities in the cold image. Next, during comparison in act 184, regardless of which image has its intensities adjusted, the adjusted intensities in the hot image are subtracted from the intensities in the cold image at corresponding locations, to obtain the results of comparison (i.e. act 184 in FIG. 1A) for each location (and the results form a differential image). Note that the subtraction can be in the opposite direction, i.e. the cold intensities may be subtracted from the adjusted hot intensities, depending on the embodiment.

In some embodiments, a comparison result at an area suspected of containing a defect is identified in act 185 (FIG. 1C) as being significantly different if it exceeds corresponding results at other areas by a predetermined value. Such an area may be found, for example, by first finding the maximum intensity in a differential image (or an averaged differential image), and then subtracting an average intensity around the location of the maximum from the maximum intensity, to obtain a difference. If such a difference exceeds a predetermined difference then the area is flagged as having a defect. Note that instead of a maximum intensity as described in this paragraph, a minimum intensity may be used in alternative embodiments (e.g. depending on the order in which the intensities of the hot and cold images are subtracted from one another). Moreover, in some embodiments, a threshold may be determined per pixel, rather than per image, by comparison of images from identical regions in adjacent dies (i.e. in a die-to-die comparison or alternatively in a cell-to-cell comparison).

Numerous embodiments based on the methods described herein will be apparent to the skilled artisan in view of the alternatives described in U.S. patent application Ser. Nos. 10/200,580 and 10/097,442. For example, in one alternative embodiment, if the maximum intensity in the differential image exceeds a predetermined maximum then the area is flagged as having a defect. In still another embodiment, the maximum intensity is not found, and instead all intensities in the differential image are compared to the predetermined maximum and if any intensity exceeds then the area is flagged as having a defect. In yet another embodiment, all intensities in the differential image are compared to one of several predetermined intensities whose value may be selected based on and responsive to the type of material expected to be present at each area.

In one example, the measured intensity has values in different ranges for different types of areas (e.g. either (a) conductive material v/s dielectric material or (b) conductive lines of different widths). Hence, the measured intensities may be classified into different ranges, thereby to identify correspondingly different types of areas in the substrate. For example, in a via chain test structure, a first metal layer at the surface of the substrate is typed differently in some embodiments from a second metal layer that is underneath the first metal layer, and two different ranges are associated with these two types of conductive materials.

In some embodiments wherein an average intensity around an area of maximum intensity is to be found, all the areas that are used in averaging the intensity are areas that have the same type of material present as the area of maximum intensity. Moreover, in some embodiments, the averaging is done only for intensities in same type areas that are immediately adjacent to (e.g. share a border with) the area of maximum intensity.

In several embodiments, after an averaged differential image is obtained from an area (by subtracting hot and cold images, and averaging their difference over a number of cycles), the entire process is repeated at one or more other areas in substrate 170. Such other areas may be identical to one another and may be located either (a) in different dies or (b) in different cells as described in U.S. application Ser. No. 10/097,442, depending on the embodiment. Averaged differential images from different dies may be compared to implement a die-to-die comparison. Alternatively, averaged differential images from different cells may be compared to implement a cell-to-cell comparison.

Specifically, in some embodiments, computer 192 is programmed to execute die-to-die, and/or die-to-database defect detection schemes. For convenience of explanation it is assumed that computer 192 executes a die-to-die defect detection scheme. In this scheme, differential images that are currently generated as a result of act 184 (of some embodiments) are compared to previously generated differential images. In an alternative die to die defect detection scheme, the differential images may be compared to other currently generated differential images. Reference differential images are generated by performing the method 180 on a reference die (e.g. on a reference substrate).

Each differential image from an area of the substrate under evaluation is compared to a corresponding reference differential image from a corresponding area in the reference substrate. Two differential images correspond if they were generated from the same relative area on the reference die and on the die undergoing evaluation. When implementing cell-to-cell comparisons, the area is relative to the cell wherein each wafer includes multiple cells, and a cell to cell comparison may involve a comparison of two cells of the same wafer that ideally have the same patterns.

The results of the comparisons between the differential image of a die undergoing evaluation and a reference differential image indicate whether or not a wafer element is suspected of being defective. The wafer element will be suspected as being defective if the difference between corresponding intensities for the wafer element in the differential images being compared exceeds a preset value.

In many embodiments, comparison of differential images is done for nominally identical wafer elements which may be located at the same area on an inspected die and a reference die, or to the same area on different patterns on the same die, respectively. Alignments to ensure that identical wafer elements are being imaged are usually made in the wafer element domain, but this is not necessarily so. Alignment methods are known in the art. An illustration of a method for such an alignment is described in U.S. Pat. Nos. 5,699,447, 5,982,921 and 6,178,257B1 of Alumot, which are hereby incorporated by reference. Another alignment method is described at U.S. Pat. No. 5,659,172 of Wagner, which is hereby incorporated by reference.

Numerous modifications and adaptations of the embodiments and examples described herein will be apparent to the skilled artisan in view of the disclosure.

For example, although in a number of embodiments described above a pump beam is used to apply heat, in other embodiments the pump beam may be used to generate excess charge carriers as described in U.S. Pat. No. 6,049,220, and the probe beam may be used to capture the distribution of excess charge carriers in a hot image, with the cold image essentially capturing the background charge carriers. In such embodiments, defects in formation of a semiconductor junction are identified. U.S. Pat. No. 6,049,220 is incorporated by reference herein in its entirety.

As another example, although in some embodiments described above a differential image is obtained by subtracting intensities (either raw or adjusted) of the cold and hot images, alternative embodiments divide an intensity at a location in one of the images by a corresponding intensity from the other of the images, thereby to obtain a ratio of intensities for each location. In such embodiments, the result of comparing is a differential image formed by such ratios at each of several locations in an area As still another example, although in some embodiments a shutter of the camera is turned off when an image is no longer being captured, in other embodiments the shutter is not turned off. Instead, although the shutter remains open, a frame grabber no longer supplies frames to the computer. Alternatively, the computer selectively uses frames that are continuously supplied by the frame grabber, e.g. only frames supplied during the time period when the shutter of the camera is otherwise kept open (to capture a hot image or a cold image).

Although in some embodiments intensities at each of uniformly spaced locations in a hot image are compared with corresponding intensities at corresponding locations in a cold image (thereby to cover the entirety of an area) in certain embodiments, only a portion of the hot image is compared to a corresponding portion of the cold image. The specific portion to be compared may be determined in any manner, e.g. (1) by a human operator identifying the portion and (2) the portion being identified by the type of material to be present at the location, being conductive material for example. In the just-described example, intensities in two images at only locations of conductive lines within an area are compared and the rest of the intensities in the two images are not used.

In some embodiments, several line images from a line camera 360 (one from each longitudinal region that is illuminated) are assembled by computer 391, into an image of the type obtained from a two-dimensional camera although such assembly is not necessary to flag a defective location. Also, note that although in some embodiments the hot and cold images are formed successively one after another at a single linear region, in other embodiments a number of hot images for assembling a hot aerial image are all imaged successively one after another, and thereafter a corresponding number of cold images are all imaged successively one after another.

Note that in some embodiments it is not necessary to switch on and off the above-described probe beam 141 (and laser 140). In such alternative embodiments, the probe beam is left on and the camera timing controls the integration. Switching the probe is performed in some embodiments because in such embodiments the user can concentrate the probe power at the appropriate time delay, limiting sample heating due to the probe and minimizing total probe intensity requirements. When these are not at issue, the probe can be left on continuously in the just-described alternative embodiments.

In several of the just-described alternative embodiments, the block diagrams for the hardware are similar or identical to FIGS. 1A, 2A and 3A except for the following difference: switching circuit 190 is decoupled from probe laser 140. Therefore, FIGS. 1A, 2A and 3A are modified by removing the line shown between switch 190 and 140 (although the line may be retained if switch 190 is configured to supply constant power/signal). Hence, timing diagrams for such alternative embodiments are similar to the timing diagrams in FIGS. 1D, 1G and 1H except that the probe beam 141 is on all the time (and hence it forms a horizontal straight line in a graph of the type shown in FIG. 1D). Note that circuit 190 instead of being physically decoupled from (i.e. not connected to) the laser 140, in alternative embodiments, circuit 190 may simply deactivate (i.e. not actively drive a signal on) the line connected to laser 140. Note that many such alternative implementations of such embodiments of the invention will be apparent to the skilled artisan in view of the disclosure.

Depending on the response time of sensors in camera 160, in the alternative embodiments camera 160 may be turned on and off at the same times as in the embodiments described in reference to FIGS. 1A–4 (e.g. turned on during the periods t3–t6 and t8–t11 in FIG. 1D). However, in some alternative embodiments camera 160 may be turned on and off closer to the times when the image is being captured (i.e. turned on during the periods t4–t5 and t9–t10) e.g. if the response time is relatively small (ideally zero).

Hence in the just-described alternative embodiments, the above-described phase difference relationships are valid, although the relationships are now between pump beam generation and camera shutter opening/closing (instead of probe beam generation). As will be apparent to the skilled artisan, the precise values of the phase differences in the alternative embodiments depend on a number of factors, such as the response time as noted above.

Specifically, switching circuit 190 of the just-described alternative embodiments implements a first phase difference between generation of the pump beam 111 and a first opening of the shutter of camera 160 (i.e. the time period t1–t3 illustrated in FIG. 1D). As noted above, the first phase difference is kept sufficiently small to ensure that sensors in camera 160 capture a hot image of the area while heat is dissipating therefrom. Switching circuit 190 of the alternative embodiments also implements a second phase difference between generation of the pump beam 111 and a second opening of the shutter of camera 160 immediately after the first generation (i.e. the time period t1–t8 also illustrated in FIG. 1D). Once again, the second phase difference is kept sufficiently large to ensure that sensors in camera 160 capture a cold image of the area, after a majority of heat applied by beam 111 is dissipated therefrom.

Numerous such modifications and adaptations of the embodiments and examples described herein are encompassed by the attached claims.

What is claimed is:

1. A method of identifying a defect in a semiconductor wafer comprising a plurality of conductive lines and a plurality of vias, the method comprising:

imaging an area directly on a top surface of the semiconductor wafer with and without application of heat directly to the top surface, to obtain a hot image and a cold image respectively;

wherein the top surface is an exposed surface of the semiconductor wafer closest to active regions therein;

repeating multiple times in a second, said imaging with and without application of heat to generate a plurality of hot images and a plurality of cold images;

comparing the plurality of hot images and said hot image with the plurality of cold images and said cold image; and identifying said defect based on the comparison.

2. The method of claim 1 further comprising, prior to said identifying:

averaging results from each comparing to obtain an averaged comparison result;

wherein said identifying uses said averaged comparison result.

3. The method of claim 1 further comprising, during said identifying:

checking if a result of comparing differs significantly relative to previous results of said comparing.

4. The method of claim 1 further comprising, during said identifying:

checking if a result of comparing exceeds a predetermined value.

5. The method of claim 4 wherein:

said predetermined value is responsive to a type of material expected to be present, and size and geometry of a feature to be fabricated.

6. The method of claim 1 further comprising:

adjusting intensities in said hot image to ensure that a majority of adjusted intensities are at least substantially same as intensities at corresponding locations in the cold image.

7. The method of claim 6 further comprising, during said comparing:

subtracting adjusted intensities for the hot image from intensities at corresponding locations in the cold image, thereby to obtain said results of said comparing for each location.

8. The method of claim 1 further comprising adjusting intensities in at least one of said hot and cold images to ensure that a majority of adjusted intensities are at least substantially same as intensities at corresponding locations in the other of said hot and cold images.

9. The method of claim 1 further comprising:

adjusting gain and offset of intensities in said images.

10. The method of claim 1 further comprising, during said comparing:

normalizing intensities in each of said hot and cold images; and subtracting normalized intensities in one of said hot and cold images from normalized intensities in the other of said hot and cold images.

11. The method of claim 1 further comprising, during said comparing:

subtracting intensities in said cold image from intensities in said hot image, thereby to obtain a difference in intensities for each location.

12. The method of claim 1 wherein:

said hot image is imaged during applying heat.

13. The method of claim 1 wherein:

said hot image is imaged immediately after said applying heat; and said cold image is imaged subsequent to imaging of said hot image but prior to applying heat again.

14. The method of claim 1 wherein:

said imaging uses a plurality of sensors located along a straight line.

15. The method of claim 14 further comprising:

repeating said imaging along a plurality of lines parallel to said straight line;

wherein each line in said plurality of lines is separated from an adjacent line in said plurality of lines by a predetermined distance.

16. The method of claim 1 wherein:

said imaging uses a plurality of sensors located in a two-dimensional plane.

17. The method of claim 1 wherein a differential image is obtained from said comparing, the method further comprising:

repeating said imaging and said comparing in corresponding areas of a plurality of dies, to obtain a differential image for each die; and making a die-to-die comparison of the differential images, to identify each defective location.

18. The method of claim 17 wherein:

for each die a plurality of differential images are obtained and averaged to obtain an averaged differential image; and the averaged differential images are compared to one another during said die-to-die comparison.

19. The method of claim 1 wherein a differential image is obtained from said comparing, the method further comprising:

repeating said imaging and said comparing in a plurality of cells, to obtain a differential image for each cell; and making a cell-to-cell comparison of the differential images, to identify each defective location.

20. The method of claim 1 wherein:

during said imaging the hot image is obtained by simultaneously making a plurality of measurements in said area to obtain a corresponding plurality of pixels for the hot image and the cold image is obtained at a different time by simultaneously making another plurality of measurements in said area to obtain another plurality of pixels for the cold image.

21. The method of claim 1 wherein:

a probe beam illuminates said area at least during imaging.

22. The method of claim 1 wherein:

the cold image is imaged only after a majority of heat is dissipated from the area.

23. A method of identifying a defect in a substrate, the method comprising:

imaging an area of the substrate with and without application of heat, to obtain a hot image and a cold image respectively;

comparing at least a portion of the hot image with a corresponding portion of the cold image; and providing an indication about a suspected defect in response to the comparison;

wherein heat is applied by a heating beam; and wherein a probe beam illuminates said area at least during imaging, said probe beam having a different wavelength than said heating beam.

24. A method of identifying a defect in a substrate, the method comprising:

imaging an area of the substrate with and without application of heat, to obtain a hot image and a cold image respectively;

comparing at least a portion of the hot image with a corresponding portion of the cold image; and providing an indication about a suspected defect in response to the comparison:

wherein heat is applied by a laser beam; and wherein said laser beam also illuminates said area at least during imaging, said laser beam having a lower intensity during illumination for imaging than during applying of heat.

25. A method of identifying a defect in a substrate, the method comprising:

heating an area of said substrate with a heating beam;

imaging said area while heat is dissipating therefrom, thereby to obtain a hot image;

imaging said area either prior to said heating or after a majority of said heat is dissipated, thereby to obtain a cold image;

wherein during at least one of said imagings, said area is illuminated by a probe beam; and comparing the hot image with the cold image to obtain a differential image;

repeating said heating, said imaging and said comparing; and averaging results of said comparing at each location across all differential images, to obtain an averaged differential image; and identifying a location as having said defect if a value in the averaged differential image at said location differs significantly relative to corresponding values at other locations.

26. The method of claim 25 wherein:

said other locations are preselected to have one of: a type of material expected to be present, size and geometry of a feature to be fabricated.

27. An apparatus for identifying a defect in a substrate, the apparatus comprising:

a heating source, for heating an area of the substrate;

an illumination source, for illuminating the area being heated by the heating source;

a plurality of sensors, for obtaining a hot image and a cold image respectively of the area; and a processor, for comparing at least a portion of the hot image with a corresponding portion of the cold image, and providing an indication about a suspected defect in response to the comparison.

28. The apparatus of claim 27 wherein said processor receives a plurality of hot and cold images for said area, said processor being programmed to:

average results of said comparing to obtain an averaged comparison result; and use said averaged comparison result to generate said indication.

29. The apparatus of claim 27 further comprising a switching circuit coupled to the heating source and the plurality of sensors, the switching circuit being configured to automatically turn on and off the heating source at a first frequency that is half of a second frequency of imaging by the plurality of sensors.

30. The apparatus of claim 29 wherein:
said switching circuit comprises an acousto-optic crystal.

31. The apparatus of claim 29 wherein:
said switching circuit comprises an electro-optic crystal.

32. The apparatus of claim 29 wherein:
said switching circuit comprises means for modulating electrical drive current to said laser.

33. The apparatus of claim 29 wherein said processor receives a plurality of hot and cold images for said area, said processor being programmed to:

average results of said comparing at each location to obtain an averaged comparison result for each location; and use said averaged comparison result during said identifying.

34. The apparatus of claim 29 wherein said illumination source comprises an arc lamp.

35. The apparatus of claim 29 wherein said illumination source comprises a laser.

36. The apparatus of claim 29 wherein said plurality of sensors are located along a straight line.

37. The apparatus of claim 29 wherein said plurality of sensors are located along a two dimensional plane, and are included in an area camera.

38. The apparatus of claim 29 wherein said plurality of sensors are included in a CCD camera, said apparatus comprising said CCD camera.

39. An apparatus for identifying a defect in a substrate, the apparatus comprising:

a first source of electromagnetic radiation;

a second source of electromagnetic radiation, the second source being located relative to the first source to illuminate an area of the substrate to be illuminated by said first source;

a plurality of photodetectors sensitive to electromagnetic radiation from the second source; and a switching circuit having a first line connected to said first source, and a second line connected to said plurality of sensors;

wherein the switching circuit supplies a first control signal on the first line to automatically turn on and off said first source at a first frequency;

wherein the switching circuit a second control signal on the second line to turn on and off the photodetectors at a second frequency, the second frequency being twice the first frequency;

wherein a first phase difference between turning on of the first source and a first turning on of the photodetectors immediately thereafter, is sufficiently small to ensure that the photodetectors capture a first image of said area while heat is dissipating therefrom; and wherein a second phase difference between turning on of the first source and a second turning on of the photodetectors immediately after the first turning on is sufficiently large to ensure that said photodetectors capture a second image of said area after a majority of said heat is dissipated therefrom.

40. The apparatus of claim 39 wherein:

the switching circuit has a third line connected to the second source of electromagnetic radiation; and the switching circuit supplies a third control signal on the third line to turn on and off the second source at the second frequency.

41. The apparatus of claim 39 wherein:

the switching circuit is decoupled from the second source of electromagnetic radiation.

42. The apparatus of claim 39 further comprising:

a computer coupled to the plurality of photodetectors to receive therefrom each of the first image and the second image;

wherein said computer is programmed to compare said first image and said second image and to identify said area as being suspected of containing said defect based on a result of comparison.

43. The apparatus of claim 39 wherein:
the switching circuit is coupled by a third line to the second source of electromagnetic radiation; and
the third line is deactivated.

44. The apparatus of claim 39 wherein said plurality of photodetectors are located along a straight line.

45. The apparatus of claim 39 wherein said plurality of photodetectors are located along a two dimensional plane, and are included in an area camera.

46. The apparatus of claim 39 wherein said plurality of photodetectors are included in a CCD camera, said apparatus comprising said CCD camera.

47. A method of evaluating a semiconductor wafer for a defect, the method comprising:

imaging an area on a top surface of the semiconductor wafer with and without heating the top surface, to obtain a hot image and a cold image respectively;

wherein the area on the top surface is illuminated with a beam of electromagnetic radiation at least when one of the hot image and the cold image are imaged; and identifying a location in the semiconductor wafer as having said defect based at least on the hot image and the cold image.

48. The method of claim 47 wherein:
an additional beam illuminates said area during heating.

* * * * *